US011534511B2

(12) United States Patent
Romo et al.

(10) Patent No.: US 11,534,511 B2
(45) Date of Patent: Dec. 27, 2022

(54) PROPORTIONALITY OF DISTRIBUTED ILLUMINATION WITH ADAPTIVE MULTIVECTOR DELIVERY SYSTEM

(71) Applicant: Leviant, Inc., Hawthorne, NY (US)

(72) Inventors: Luis F. Romo, New York, NY (US); Wladyslaw Kowalski, Long Island City, NY (US); Audrey McNicholas, Long Island City, NY (US); Arto Cinoglu, Bohemia, NY (US); David Moses, Bohemia, NY (US)

(73) Assignee: Leviant, Inc., Hawthorne, NY (US)

( * ) Notice: Subject to any disclaimer, the term of this patent is extended or adjusted under 35 U.S.C. 154(b) by 0 days.

(21) Appl. No.: 17/708,238

(22) Filed: Mar. 30, 2022

(65) Prior Publication Data

US 2022/0218856 A1     Jul. 14, 2022

Related U.S. Application Data

(63) Continuation of application No. PCT/US2020/063669, filed on Dec. 7, 2020.

(60) Provisional application No. 62/944,686, filed on Dec. 6, 2019.

(51) Int. Cl.
| | |
|---|---|
| *A61L 2/10* | (2006.01) |
| *A61L 2/24* | (2006.01) |
| *B08B 7/00* | (2006.01) |
| *A61L 2/26* | (2006.01) |

(52) U.S. Cl.
CPC ............... *A61L 2/10* (2013.01); *A61L 2/24* (2013.01); *A61L 2/26* (2013.01); *B08B 7/0057* (2013.01); *A61L 2202/11* (2013.01); *A61L 2202/14* (2013.01); *A61L 2202/25* (2013.01)

(58) Field of Classification Search
None
See application file for complete search history.

(56) References Cited

U.S. PATENT DOCUMENTS

| | | | |
|---|---|---|---|
| 4,448,750 | A | 5/1984 | Fuesting |
| 5,080,209 | A | 1/1992 | Yurko |
| 5,145,366 | A | 9/1992 | Janhuen |
| 5,272,848 | A | 12/1993 | Maas |
| 5,533,305 | A | 7/1996 | Bielecki |

(Continued)

FOREIGN PATENT DOCUMENTS

| | | |
|---|---|---|
| AU | 2013361188 A | 7/2015 |
| AU | 2013361188 B2 | 5/2017 |

(Continued)

OTHER PUBLICATIONS

International Search Report and Written Opinion in PCT International Application No. PCT/US2020/063669 dated Mar. 10, 2021.

*Primary Examiner* — Andrew Smyth

(57) ABSTRACT

An ultraviolet emitting device comprising a plurality of light sources; and a plurality of arms on which the plurality of light sources are mounted, wherein: each arm is expandable between a first position and a second position, each arm is fully collapsed in the first position and fully expanded in the second position, and when each arm is transitioning between the first position and the second position, a length of the arm maintains a fixed proportionality with respect to a spacing of the plurality of light sources on the arm.

9 Claims, 18 Drawing Sheets

(56) References Cited

U.S. PATENT DOCUMENTS

| | | |
|---|---|---|
| 5,891,399 A | 4/1999 | Owesen |
| 7,829,016 B2 | 11/2010 | Deal et al. |
| 8,067,750 B2 | 11/2011 | Deal |
| 9,107,973 B1 | 8/2015 | Robinson et al. |
| 9,675,720 B2 | 6/2017 | Romo et al. |
| 10,376,604 B2 | 8/2019 | Romo et al. |
| 10,894,102 B2 | 1/2021 | Romo et al. |
| 2002/0085947 A1 | 7/2002 | Deal |
| 2003/0018373 A1 | 1/2003 | Eckhardt et al. |
| 2003/0202902 A1 | 10/2003 | Elliott |
| 2004/0056201 A1 | 3/2004 | Fink et al. |
| 2005/0201910 A1 | 9/2005 | Shou et al. |
| 2006/0175554 A1 | 8/2006 | Riddell |
| 2007/0157385 A1 | 7/2007 | Lemire et al. |
| 2007/0194255 A1 | 8/2007 | Garcia et al. |
| 2007/0274879 A1 | 11/2007 | Millikin |
| 2008/0056933 A1 | 3/2008 | Moore et al. |
| 2008/0178543 A1 | 7/2008 | Maas |
| 2009/0272029 A1 | 11/2009 | Aiking et al. |
| 2011/0044848 A1 | 2/2011 | Wright |
| 2011/0169646 A1 | 7/2011 | Raichman |
| 2011/0172810 A1 | 7/2011 | Raichman |
| 2011/0215261 A1 | 9/2011 | Lyslo et al. |
| 2011/0243789 A1* | 10/2011 | Roberts ............... A61L 2/10 422/116 |
| 2011/0259864 A1 | 10/2011 | Galietti |
| 2012/0074334 A1 | 3/2012 | Milligan |
| 2013/0002445 A1 | 1/2013 | Stibich et al. |
| 2014/0241941 A1* | 8/2014 | Kreitenberg ............. A61L 2/10 250/492.1 |
| 2015/0064065 A1* | 3/2015 | Kreitenberg ............. B25J 5/007 422/24 |
| 2015/0086420 A1* | 3/2015 | Trapani ............... A61L 9/20 422/24 |
| 2015/0192689 A1 | 7/2015 | Li et al. |
| 2015/0209458 A1* | 7/2015 | Kreitenberg ............. B64F 5/30 422/24 |
| 2015/0209459 A1* | 7/2015 | Kreitenberg ............. A61L 2/10 250/492.1 |
| 2015/0209460 A1* | 7/2015 | Kreitenberg ............. A61L 2/10 422/24 |
| 2015/0246148 A1 | 9/2015 | Blechschmidt et al. |
| 2015/0367008 A1 | 12/2015 | Romo et al. |
| 2016/0021860 A1 | 1/2016 | Fortney |
| 2016/0128526 A1 | 5/2016 | Dobrinsky et al. |
| 2016/0136314 A1* | 5/2016 | Kreitenberg ............. A61L 2/10 250/492.1 |
| 2016/0354503 A1 | 12/2016 | Hutchens et al. |
| 2017/0112953 A1* | 4/2017 | Dayton ............... G08C 17/02 |
| 2017/0112954 A1* | 4/2017 | Dayton ............... A61L 9/20 |
| 2017/0216468 A1 | 8/2017 | Romo et al. |
| 2017/0304473 A1* | 10/2017 | Farren ............... H01J 37/244 |
| 2017/0367785 A1 | 12/2017 | Munari |
| 2018/0140727 A1 | 5/2018 | Romo et al. |
| 2018/0256764 A1* | 9/2018 | Kreitenberg ............. A61L 9/20 |
| 2019/0365938 A1 | 12/2019 | Romo et al. |

FOREIGN PATENT DOCUMENTS

| | | | |
|---|---|---|---|
| AU | 2017213522 B2 | 8/2017 | |
| CN | 2155875 Y | 2/1994 | |
| CN | 2621044 Y | 6/2004 | |
| CN | 2688291 Y | 3/2005 | |
| DE | 20016160 U1 | 11/2000 | |
| EP | 2934606 A | 10/2015 | |
| EP | 2772272 B1 | 3/2017 | |
| EP | 3354289 A | 8/2018 | |
| JP | 04091794 U | 8/1992 | |
| JP | H07289616 A | 11/1995 | |
| JP | 2001327590 A | 11/2001 | |
| JP | 2005168858 A | 6/2005 | |
| JP | 63853632 A | 3/2016 | |
| JP | 2016506274 A | 3/2016 | |
| JP | 2017532138 A | 11/2017 | |
| WO | 199317195 | 9/1993 | |
| WO | 199639820 A1 | 12/1996 | |
| WO | 2001051098 A1 | 7/2001 | |
| WO | 2008010684 A1 | 1/2008 | |
| WO | 2010115183 A1 | 10/2010 | |
| WO | 2012142427 A1 | 10/2012 | |
| WO | 2014100493 A1 | 6/2014 | |
| WO | 2015012592 A1 | 1/2015 | |
| WO | WO-2016164364 A1 * | 10/2016 | ............. A61L 2/10 |
| WO | 2019143699 A9 | 8/2019 | |

\* cited by examiner

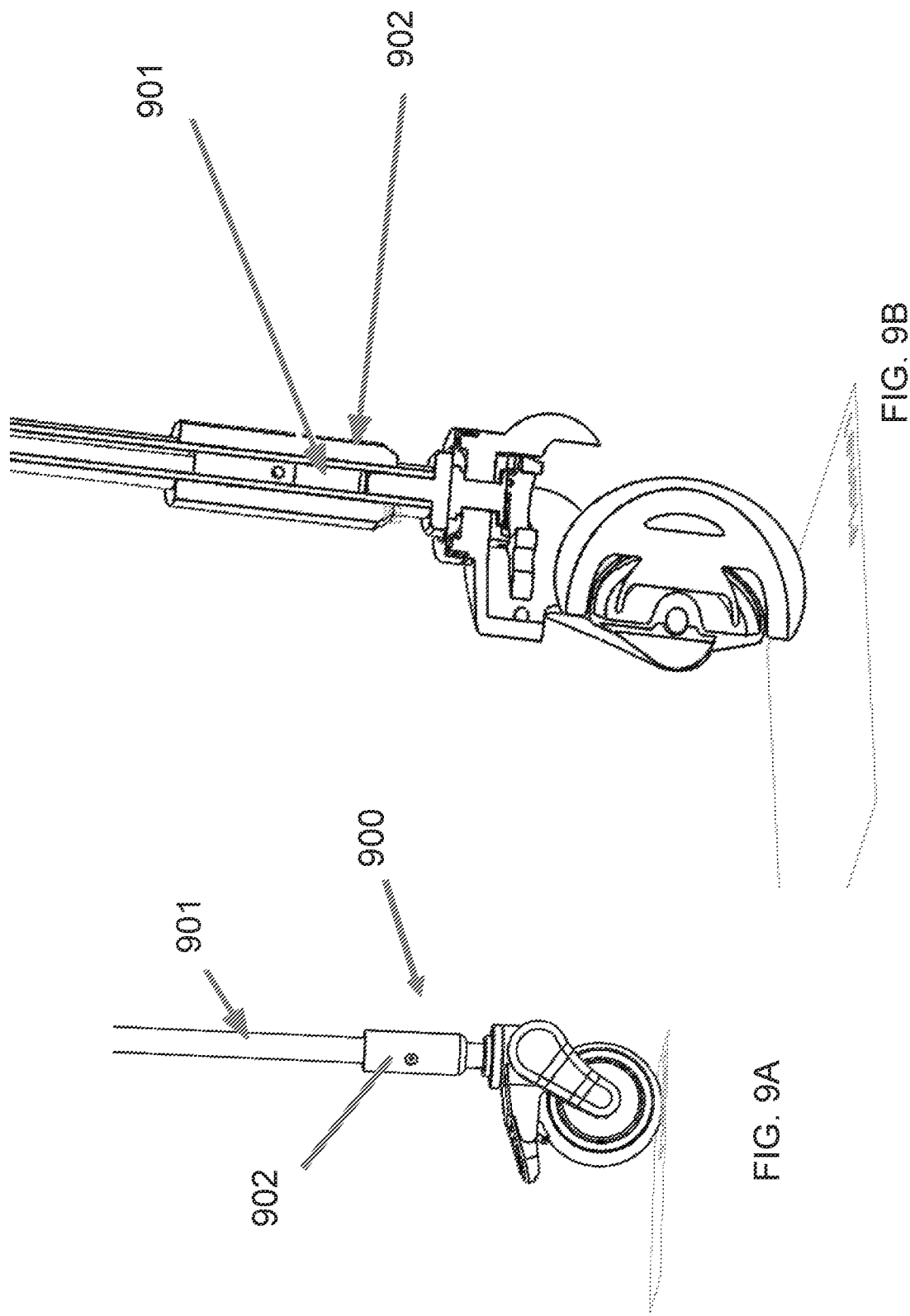

PROPORTIONALITY OF DISTRIBUTED ILLUMINATION WITH ADAPTIVE MULTIVECTOR DELIVERY SYSTEM

RELATED APPLICATION

This patent application is a U.S. Continuation Patent Application of PCT International Application No. PCT/US2020/063669, filed Dec. 7, 2020, which claims the benefit of and priority to U.S. Provisional Patent Application Ser. No. 62/944,686, filed on Dec. 6, 2019, each of which is hereby incorporated by reference herein in their entireties.

BACKGROUND

The present application generally relates to medical systems, devices and methods, and more particularly relates to the sanitization, disinfection, and sterilization of medical systems, medical devices, and areas or spaces of medical facilities and other areas where the control and prevention of disease or infection is desired. Sanitization may formally describe the use of agents that reduce microbial contaminants to safe levels. Disinfection may refer to a process that eliminates many or all pathogenic microorganisms, on inanimate objects. Sterilization may formally define a validated process used to render a product free of all forms of viable microorganisms. A surface is defined as sterile if it is free from all living microorganisms, but the verification of sterility is subject to limitations of test sensitivity and practicality.

Microbial contamination is a global concern within many industries, especially in the healthcare industry. The financial cost can amount to billions of dollars in expenses per year, and, more importantly, the contaminant pathogens plague private and public (e.g. healthcare) settings and surroundings. These contaminated surroundings can lead to infections and may ultimately cause deaths. Furthermore, many communicable diseases are transmitted through contact with contaminated areas and surfaces. The types and seriousness of communicable diseases transmitted in this manner are varied. For example, viral, fungal, and bacterial diseases alike can be communicated by physical contact with surfaces upon which the infectious agents may reside or settle. Further, there is an increasing awareness and concern worldwide of the possibility of widespread outbreaks, or even pandemics, of communicable disease; these concerns stem in part from possible spontaneous mutations of influenza and other viruses, and emergence of new diseases as well as the increasing resistance of bacterial strains to conventional and even to newly-developed and powerful antibiotics.

SUMMARY

In one aspect, some implementations provide a ultraviolet emitting device comprising: a plurality of light sources; and a plurality of arms on which the plurality of light sources are mounted, wherein: each arm is expandable between a first position and a second position, each arm is fully collapsed in the first position and fully expanded in the second position, and when each arm is transitioning between the first position and the second position, a length of the arm maintains a fixed proportionality with respect to a spacing of the plurality of light sources on the arm.

Implementations may include one or more of the following features. The plurality of arms may be capable of expanding and contracting independently of one another. The plurality of arms may be capable of rotating around a fixed axis independently of one another. The plurality of arms may each have a rotational range of up to 360 degrees. The plurality of arms may be connected to a center column.

The plurality of light sources may be split between two or more sets of horizontal scissors arms of each arm, wherein the two or more sets of horizontal scissors arms are of identical size and shape. The two or more sets of horizontal scissors arms may be configured to move in unison when each arm is expanding from the first position to the second position. The two or more sets of horizontal scissor arms of each arm may be connected at a matching set of intersections such that the fixed proportionality with respect to the spacing of the plurality of light sources are maintained when the arm is transitioning between the first position and the second position. The matching set of intersections may include bushings that facilitate each arm in transitioning between the first position and the second position.

The ultraviolet emitting device may further include: one or more motion sensors configured to detect a motion within a target volume in which the ultraviolet emitting device is located such that the ultraviolet emitting device can be deactivated from emitting ultraviolet light. The motion sensors may provide full coverage of the target volume in which the ultraviolet emitting device is located, and wherein a first subset of motion sensors are configured to face outward from a center column and a second subset of motion sensors are oriented face downwards from a upper portion of the center column.

The ultraviolet emitting device may further include: a wireless communication module configured to receive wireless instructions for one or more operations of the ultraviolet emitting device; a controller coupled to the wireless communication module and configured to process instructions to control the one or more operations of the device; and a user panel configured to include an option for remote operation of the ultraviolet emitting device.

The ultraviolet emitting device may further include: a camera configured to monitor a surrounding of the ultraviolet emitting device such that a remote viewing of the surrounding of the ultraviolet emitting device is accessible from outside a target volume in which the ultraviolet emitting device is located.

In another aspect, some implementations provide a system that includes: a structure configurable to irradiate a target volume, wherein the structure includes: a movable base including a holding bracket having a slot; a plurality of arms connected to an anchor surface, each arm configurable between a first position and a second position, wherein the arm is fully collapsed in the first position and fully expanded in the second position; a support connected to at least one arm of the plurality of arms, the support including an inner shaft capable of radially fitting into the slot of the holding bracket; and a collar connected to the support and axially adjustable within the slot of the holding bracket, wherein the holding bracket configured to restrict a radial movement of the collar to within the slot of the holding bracket; and a plurality of light sources connected to the plurality of arms and capable of emitting ultraviolet light to irradiate the target volume when the arms of the structure are positioned in-between the first position and the second position.

In yet another aspect, some implementations provide a system that includes: a structure positionable within a target volume, the structure including: a base; and a plurality of arms connected to the base, each arm configurable between a first position and a second position, wherein the arm is fully collapsed in the first position and fully expanded in the second position; a plurality of light sources connected to the plurality of arms and capable of emitting ultraviolet light to irradiate the target volume when the arms of the structure are positioned between the first position and the second position; and a motion sensor connected to a top portion of the structure.

Implementations may include one or more of the following features.

The motion sensor may be mounted upside down capable of providing a sensing range of up to 360 degrees. The system may further include a plurality of supports extending from the top portion of the structure and configured to hold the motion sensor when the arms of the structure are transitioning between the first position and the second position.

In still another aspect, some implementations provide a method that includes: unlocking a plurality of expandable arms on which a plurality of light sources are mounted; expanding the plurality of expandable arms from a first position towards a second position, wherein each expandable arm is fully collapsed in the first position and fully expanded in the second position collapsed position; and activating the plurality of light sources to emit ultraviolet light to irradiate a target volume.

Implementations may include one or more of the following features.

Expanding the plurality of expandable arms may include: rotating at least one of the plurality of expandable arms with respect to an attachment point at a center column where the plurality of expandable arms are connected to the center column. The method may further include: when expanding the plurality of expandable arms, maintaining an identical angle between two or more sets of horizontal scissors arms of each expandable arm such that the light sources on each expandable arm are identically spaced. Expanding the plurality of expandable arms may include: moving two or more sets of horizontal scissors arms of each expandable arm in unison. The method may further include: contracting the plurality of expandable arms towards the first position in which each expandable arm is fully collapsed. Contracting the plurality of expandable arms may further comprise: moving two or more sets of horizontal scissors arms of each expandable arm in unison. A spacing between the light sources on each expandable arm may be proportional to a length of each expanded arms when the plurality of expandable arms are transitioning between the first position and the second position.

Implementations according to the present disclosure may be realized in computer implemented methods, hardware computing systems, and tangible computer readable media. For example, a system of one or more computers can be configured to perform particular actions by virtue of having software, firmware, hardware, or a combination of them installed on the system that in operation causes or cause the system to perform the actions. One or more computer programs can be configured to perform particular actions by virtue of including instructions that, when executed by data processing apparatus, cause the apparatus to perform the actions.

The details of one or more implementations of the subject matter of this specification are set forth in the description, the claims, and the accompanying drawings. Other features, aspects, and advantages of the subject matter will become apparent from the description, the claims, and the accompanying drawings.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various configurations discussed in the present document.

FIG. 9A is an isometric view of an outer vertical arm locking mechanism, in accordance with one example of the present disclosure.

FIG. 9B is a cross sectional view of FIG. 9A, in accordance with one example of the present disclosure.

Like reference numbers and designations in the various drawings indicate like elements.

DETAILED DESCRIPTION

Facilities of dynamic environments are witnessing an increasing demand for devices and systems that can adapt to a variety of situations for sterilization or disinfection of both equipment and physical rooms or spaces. For rooms with varying shapes and sizes, variability becomes abundant with respect to volume of space, equipment, and surfaces. Such variabilities call for reliable automated systems that can accommodate the differences and provide a solution with repeatable, predictable, and adaptable performance.

Some disinfection technologies that utilize ultraviolet technologies or area ultraviolet disinfection units may not expand and adapt to various types, sizes and shapes of rooms in healthcare or other environments. For example, these technologies may not eliminate shadowing effects unless the same unit is used in multiple locations with multiple exposure cycles. Such a process would defeat the purpose of expedient disinfection and would end up depending on user positioning and therefore would not be an automated process. As such, there is a need for an adaptable system capable of providing rapid disinfection that is free from the effects of shadowing.

Some area ultraviolet disinfection units can use a "one size fits all" approach in which only the position or number of units are adaptive. The limited adaptability fails to adaptively scale to meet the demand for an adequate coverage for rooms with a variety of sizes or shapes.

Healthcare facilities often struggle to control and eliminate bacteria, spores, viruses, fungi, and other harmful organisms from spaces and surfaces. Notably, many disinfection technologies that utilize ultraviolet technologies or area ultraviolet disinfection units may not achieve the performance levels, for example, with respect to proper coverage and exposure to all surfaces that may be necessary to eradicate surface-borne pathogens in such medical facilities. Additionally, the repeatability of the solution becomes desirable because such a solution can adapt to and disinfect a variety of situations, spaces, and dimensions.

Implementations of the present disclosure can leverage a proportionality of ultraviolet (UV) light sources (e.g., lamps) within a robust system to achieve adaptability, repeatability, and uniformity. Some implementations may pair an engineered system for uniform light distribution with precise placement of lamps. The implementations may incorporate a system for use by an average staff member for daily operations. The system can be sturdy and can house UV light sources in a secure fashion, while illuminating the space to be treated. In these implementations, the strength of the proportional distances can be enforced with two or more sets of horizontal scissor arms for each expandable arm. The number of UV light sources, the lengths of the scissor mechanisms and distances can be set in accordance with desired spacing of UV light sources, often mounted on each expandable arm.

Figure 1:
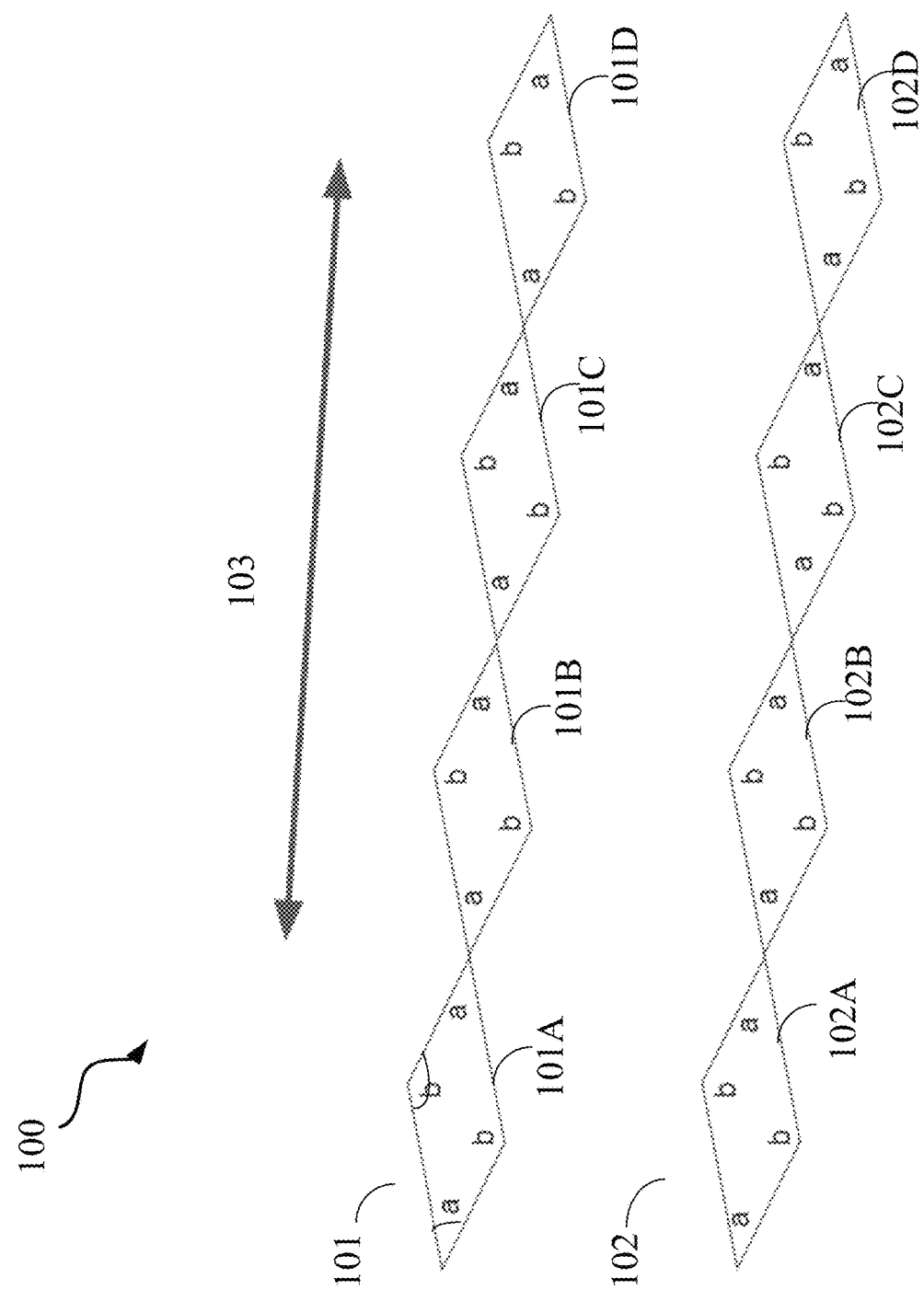
FIG. 1 shows a schematic view of two parallel horizontal scissor mechanisms which expand and contract simultaneously, in accordance with one example of the present disclosure.

FIG. 1 shows a diagram 100 that includes two parallel horizontal scissors arms, namely scissors arm 101 and scissors arm 102. Each arm is expandable. For example, both scissors arm 101 and scissors arm 102 can expand and contract simultaneously along the direction of 103. Scissors arm 101 includes four exemplary trapezoidal scissor mechanisms, namely 101A, 101B, 101C, and 101D. Similarly, scissors arm 102 includes four exemplary trapezoidal scissor mechanisms, namely 102A, 102B, 102C, and 102D. Each trapezoidal scissor mechanism is constructed by two pairs of parallel edges. The vertices of each trapezoidal scissor mechanism are characterized by angle a, and angle b, which are consistent throughout the trapezoidal scissor mechanisms. Notably, angles a and b will add up to 180 degrees regardless of level of expansion or contraction of each trapezoidal scissor mechanism. In other words, despite an infinite number of linkages for these trapezoidal scissor mechanisms, angles a and b are consistent through these trapezoidal scissor mechanisms. The sum of the angles, a+b, is maintained at 180 degrees. There could be additional trapezoidal scissor mechanisms linked to one another, in multiple layers on top of one another. In this diagram, UV light sources can be mounted on the vertices of each trapezoidal scissor mechanism. For example, UV light sources can be mounted on the vertices characterized by angle b.

Figure 2A:
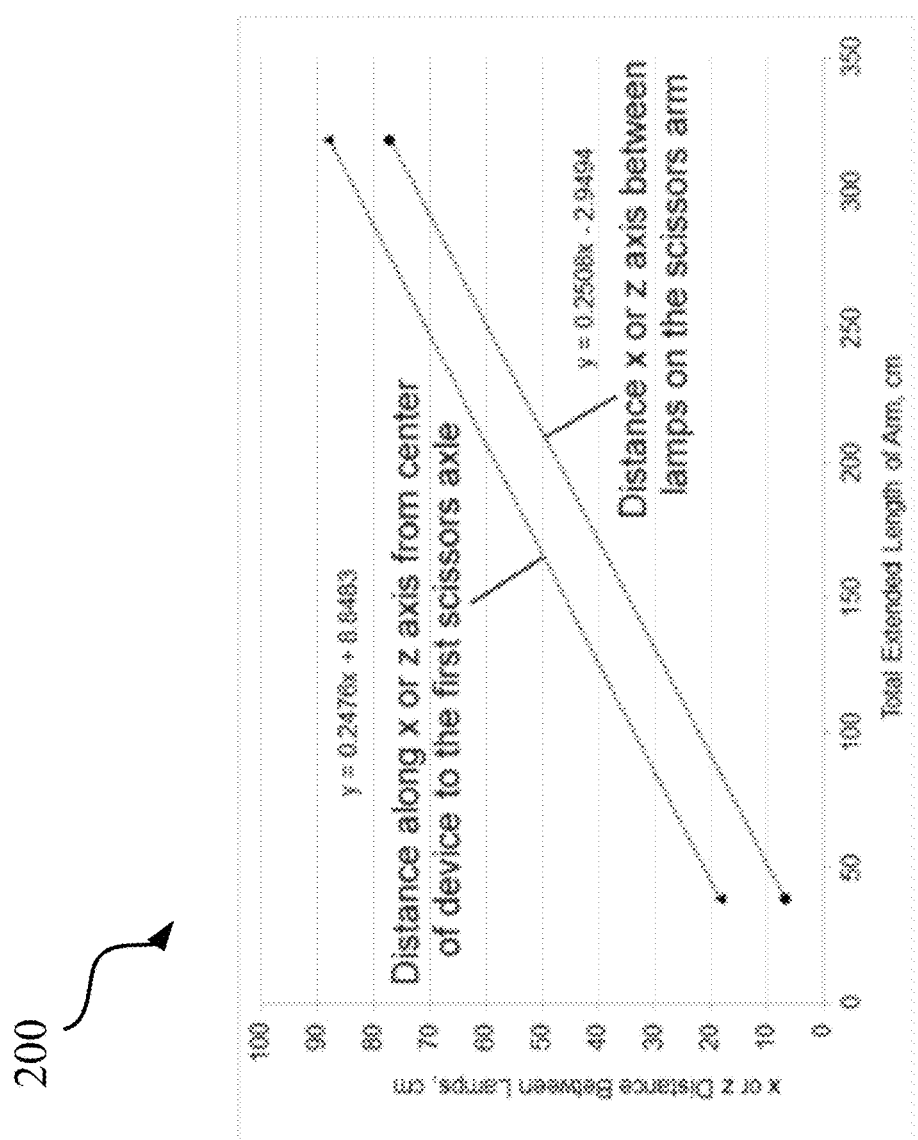
FIGS. 2A to 2B show lines of linearity as applied to the distances between the lamps when the arms of a configuration are expanded in accordance with one example of the present disclosure.
Figure 2B:
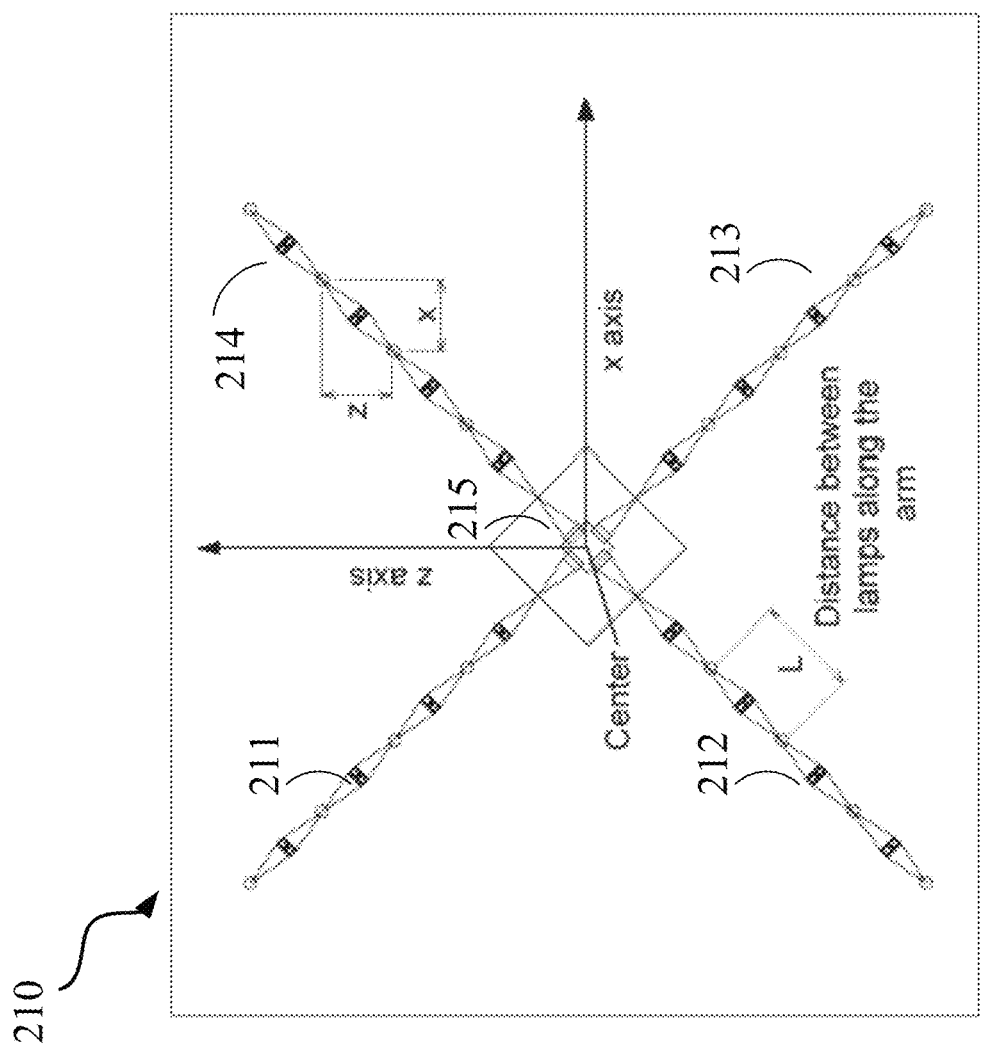

FIGS. 2A and 2B illustrate applying equations in the format of $y=mx+n$ the spacing between the UV light sources when each expandable arm is being expanded or contracted. Specifically, FIG. 2A shows an example graph 200 that includes a plot of the distance from the center of an UV treatment system to the first scissors axle (vertical axis) as a function of the length of the expandable arm (horizontal axis). Graph 200 also includes a plot of the spacing between UV light sources (vertical axis) as a function of the length of the expandable arm (horizontal axis). In each case, the linear equation describing the linear relationship is demonstrated. The linearity is regardless of the level of expansion or contraction of each expandable arm. For context, the lower limit of expansion for each arm is the collapsed condition in which the expandable arm is fully compressed. This lower limit is represented by the markers indicating the minimum dimensions. The upper limit of expansion for each arm is the fully extended condition in which the expandable arm is fully unfolded and stretched. This upper limit is represented by markers indicating the maximum dimensions, which can reach a different sized distance between the axes.

FIG. 2B shows a diagram 210 illustrating the orthogonal x or z axis, the distance from the center of the system to the first scissors axle, as well as the spacing distance between UV light sources on each expandable arm. Here, diagram 210 shows a top down view of expandable arms 211, 212, 213, and 214. Each of expandable arms 211, 212, 213, and 214 includes four trapezoidal scissors mechanisms, as explained in more detail in FIG. 1. Here, expandable arms 211, 212, 213, and 214 are connected at center 215. Here, L illustrates an example of a spacing distance between UV light sources on expandable arm 212. The x axis is horizontal in this example while the z axis is vertical in this example. In each case the linear equation describing the linear relationship is shown as an example in FIG. 2A.

Figure 3:
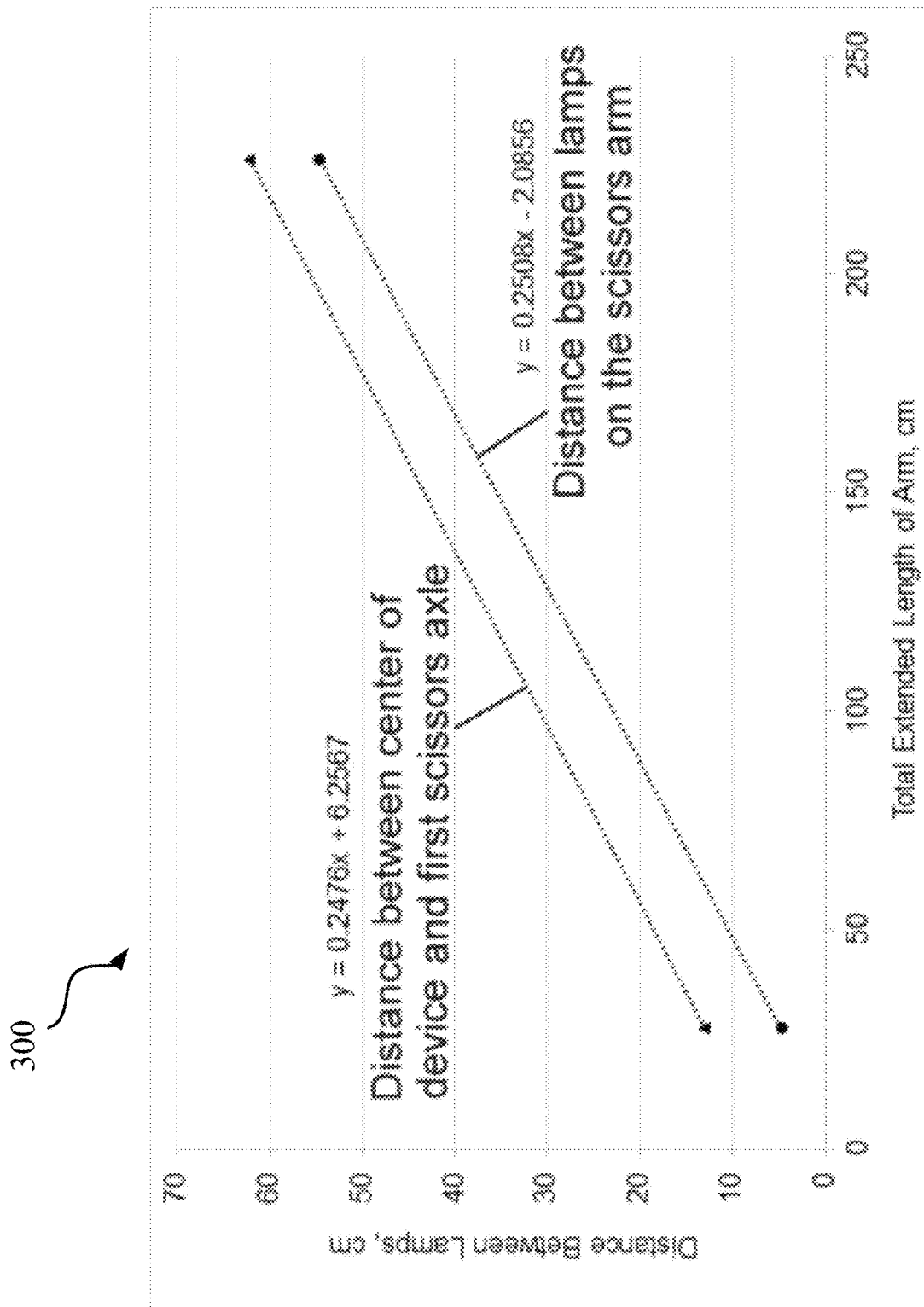
FIG. 3 shows a plot of linearity of a reference frame with axes in relation to the center of the ultraviolet emitting device, in accordance with one example of the present disclosure.

FIG. 3 shows a graph 300 which illustrates linear proportionality in relation to another example of the system for treating a target volume. This system likewise include expandable arms that can extend towards the corners of rectangular rooms. Leveraging the same trapezoidal scissors mechanism, the expandable arms can likewise expand or contract. The spacing distance between the UV light sources along the expandable arm likewise have the fixed linear proportionality with respect to the total length of each expandable arm as the arm is adjusted in distance. Here, the length of each expandable arm is presented on the hypothetical horizontal axis while the distance between UV light sources on the scissors arm is presented on the hypothetical vertical axis. In one plot, the distance between center of the system and the first scissor axle is presented on the hypothetical vertical axis.

Figure 4A:
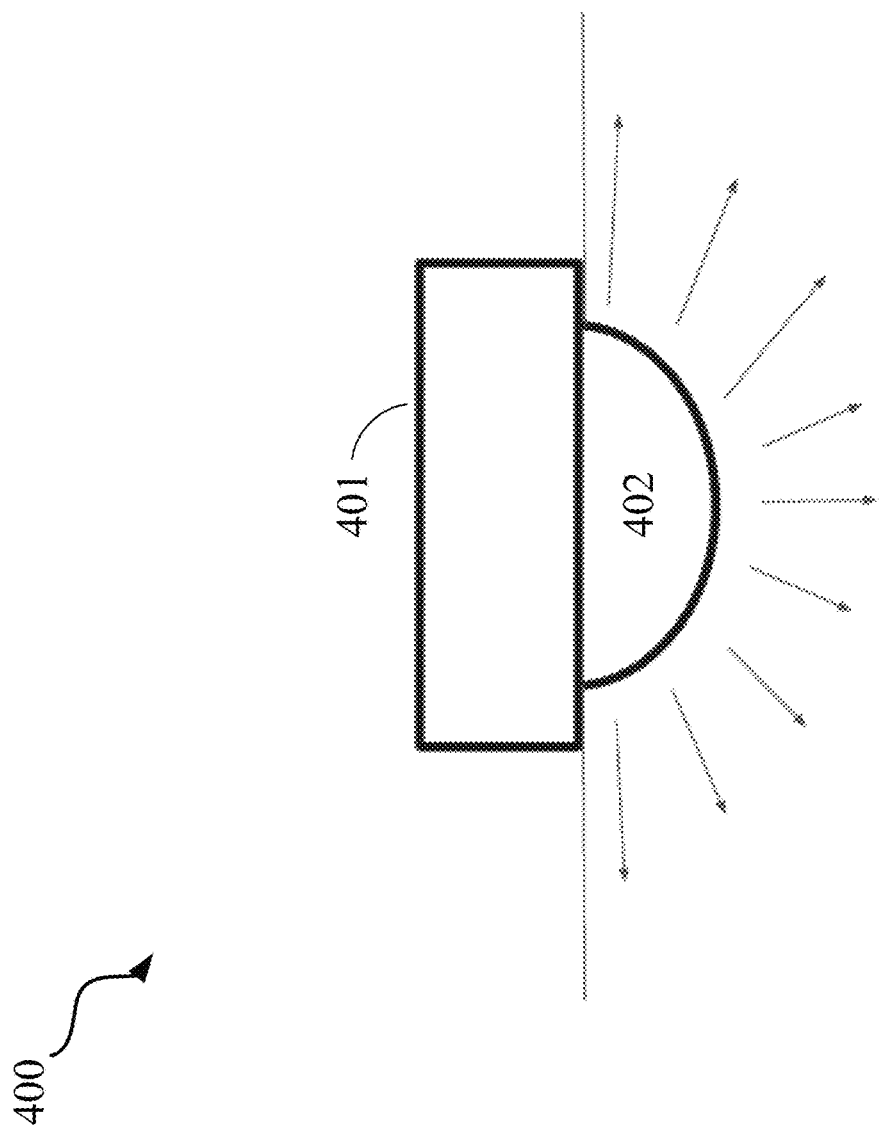
FIG. 4A shows a configuration of a motion sensor mounted to face down from a center of a system, in accordance with one example of the present disclosure.

FIG. 4A shows a diagram illustrating a mount 401 and a motion sensor 402 placed on mount 401 to face downward. As illustrated, motion sensor 402 looks down and can provide a 360 degree coverage to monitor the target volume (for example, a room). Motion sensor 402 installed in this manner can sense from all directions from the 360 degree coverage. Indeed, this 360 degree configuration can adapt to a variety of shapes or configurations of the room being targeted for treatment.

Figure 4B:
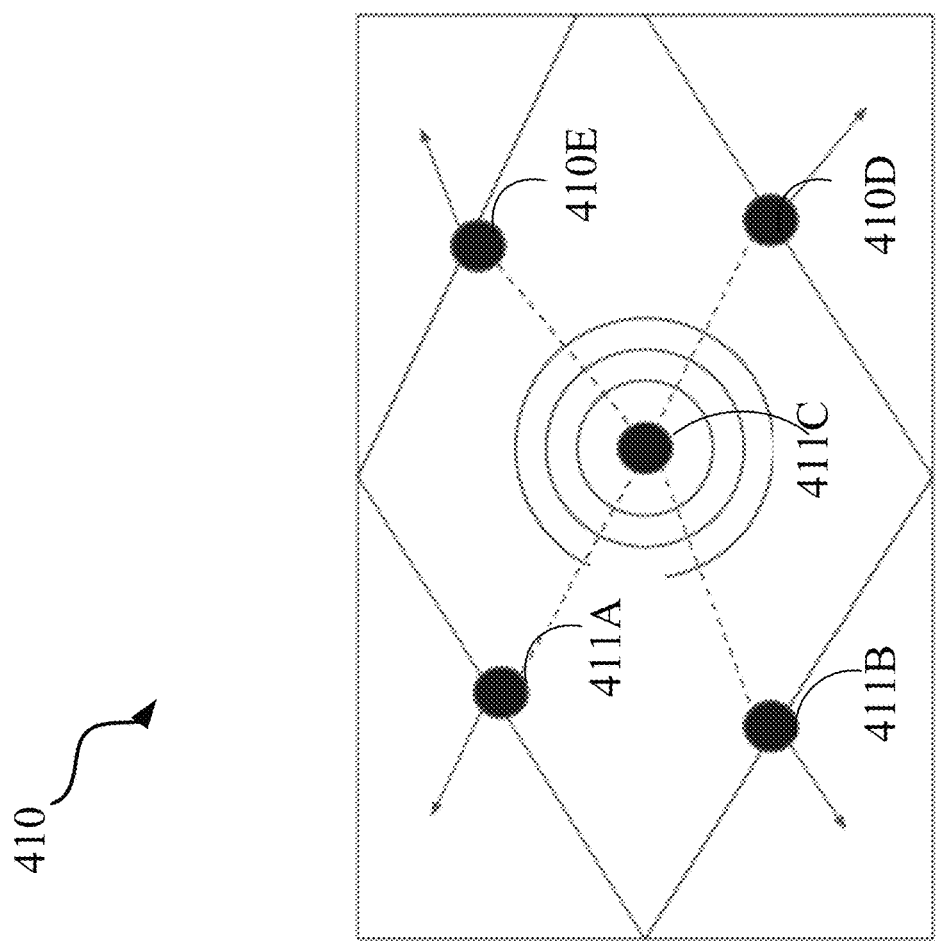
FIG. 4B shows a top view of a room with five motion sensors installed, including one referenced in FIG. 4A at the center of the room, in accordance with one example of the present disclosure.

FIG. 4B illustrates a top view 410 of a room being targeted for treatment. In this view, motion sensor 411C referenced in FIG. 4A is placed at the center of the room to provide 360 degree coverage. Additionally, four motion sensors, namely motion sensor 411A, motion sensor 411B, motion sensor 411C, and motion sensor 411D, are each attached to an expandable arm connected to a center structure. Motion sensors 411A to 144D are configured to point at the walls of the room (or perimeters of the target volume) for complete coverage. The system could deploy additional motion sensors to ensure coverage in any type, shape, or sized room.

Figure 4C:
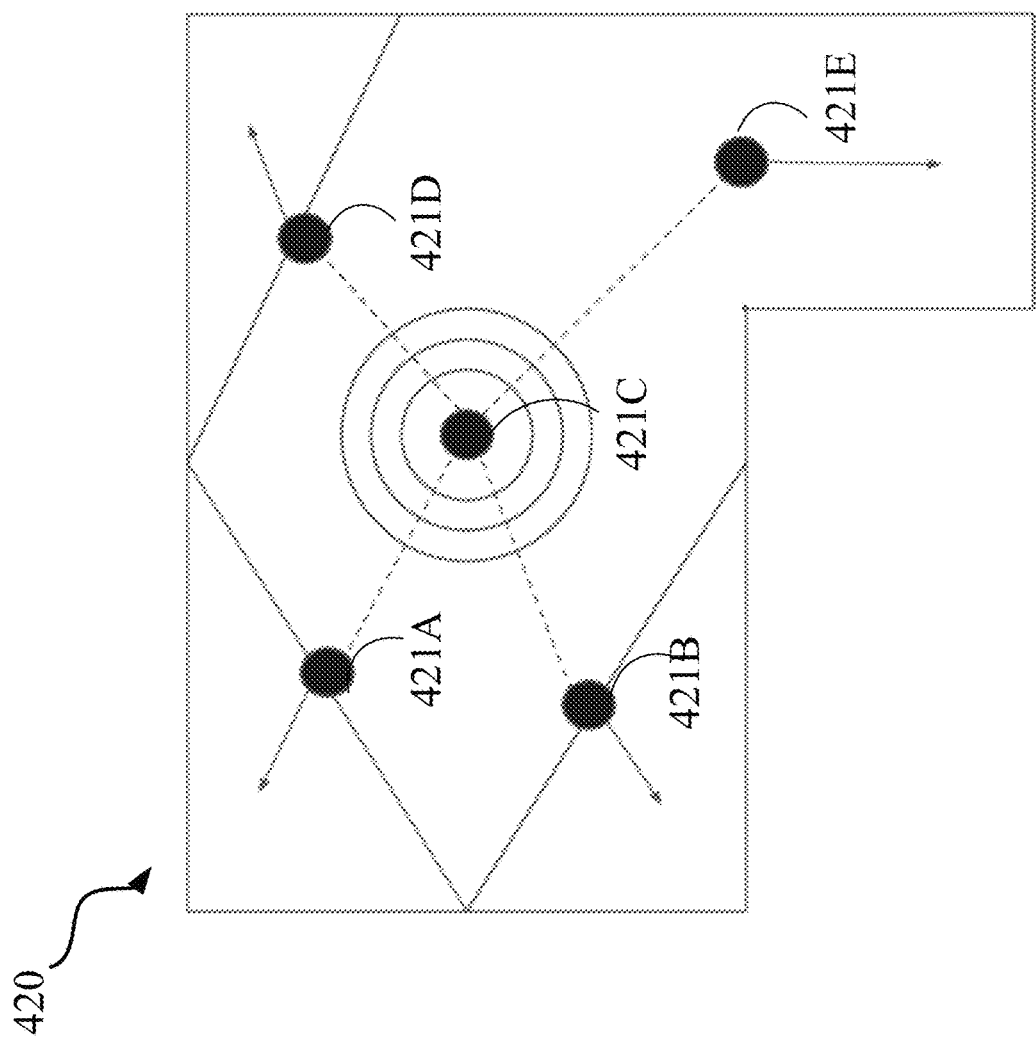
FIG. 4C shows a top view of an irregularly-shaped room with five motion sensors installed, in accordance with one example of the present disclosure.

FIG. 4C illustrates another top view 420 over an irregularly-shaped room with a passageway, such as a doorway. In this view, motion sensor 421C, although located at the center of the room to provide 360 degree coverage, may not be sufficient capture movement in this target volume. With motion sensors 421A, 421B, 421D, and especially 421E, complete coverage for the entire target volume, including the doorway area, may be achieved to provide for monitoring of motion throughout.

Figure 4D:
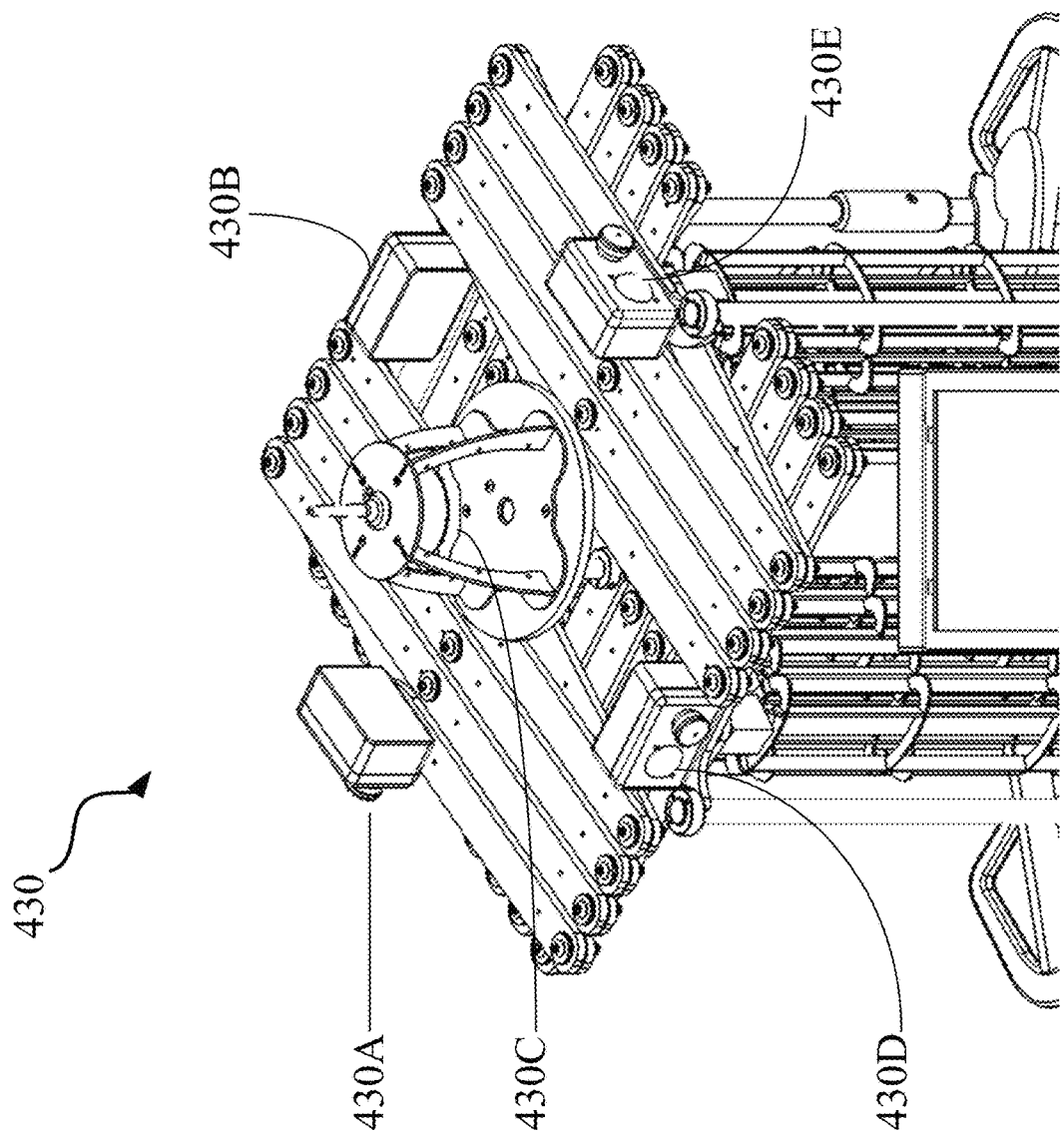
FIG. 4D shows a perspective view of a system that includes a motion sensor, in accordance with one example of the present disclosure.

FIG. 4D illustrates a perspective view 430 of an exemplary system with all four expandable arms folded and locked into a base of the exemplary system. As illustrated, motion sensors 430A, 403B, 430D, and 430E are located at the top end of each expandable arm. Each of motions sensors 430A, 403B, 430D, and 430E are pointed away from the center of the exemplary system. In other words, when the expandable arms are being expanded from the collapsed position, the motion sensor will remain at the far end of each expandable arm. At this arrangement, motions sensors 430A, 403B, 430D, and 430E can sense motion beyond the arms. Additionally, motion sensor 430C can be mounted at the top center of the system to face downward. This arrangement can create a 360 degree field of motion sensing. As describes in FIGS. 4B and 4C, this configuration can allow for full room coverage regardless of room shape or size.

Figure 4E:
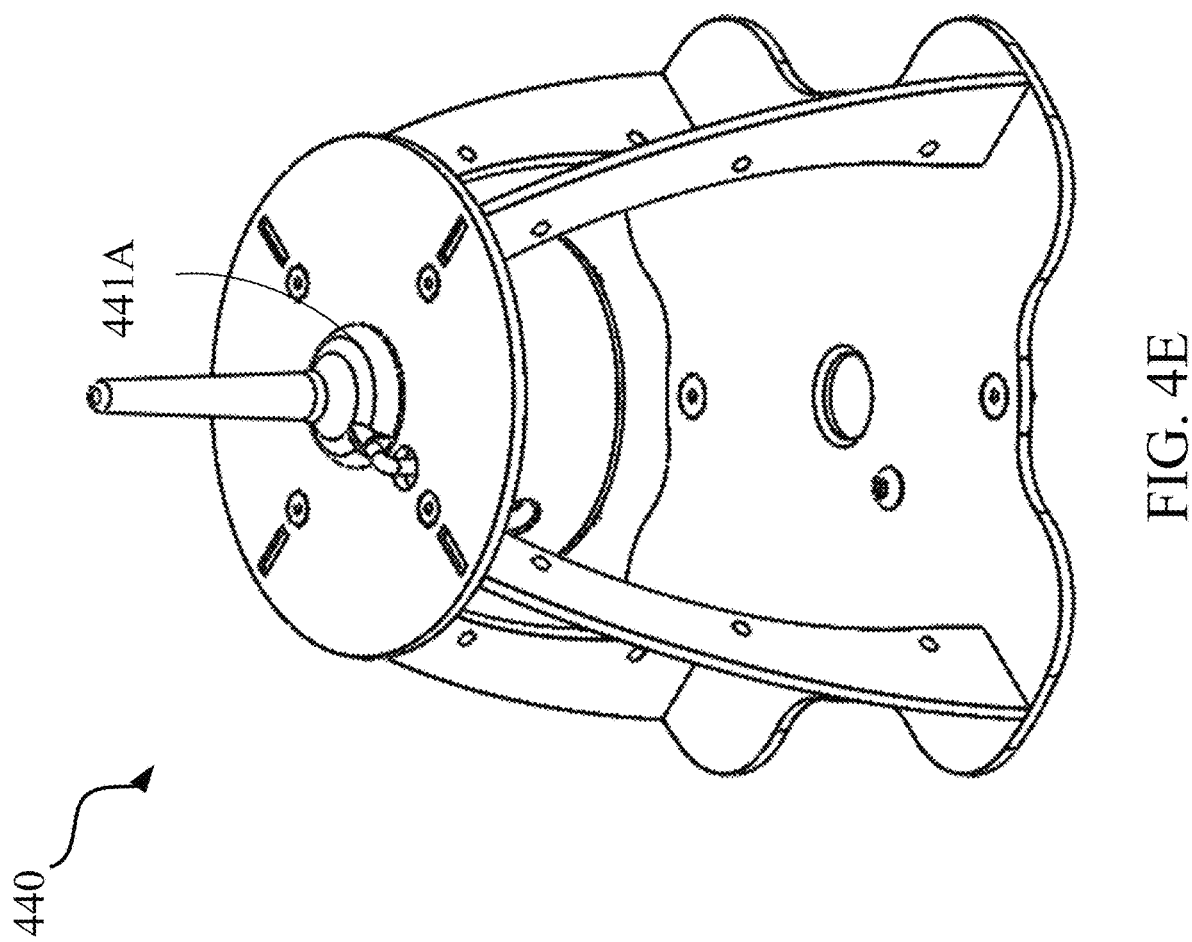
FIG. 4E shows another perspective view of a portion of a system that includes a 360 degree motion sensor, in accordance with one example of the present disclosure.

FIG. 4E illustrates a perspective view 440 of the mounting block which allows for the motion sensor 430C to be mounted upside down and provide a 360-degree range of motion sensing. The mounting block can have a flat section on the upper roof 441A with a cutout for the motion sensor dome to be mounted there. Some implementations can include additional supports holding motion sensor 430 above the top of the center unit in order to reduce blocking of certain sections of sensing (or detecting).

Figure 5A:
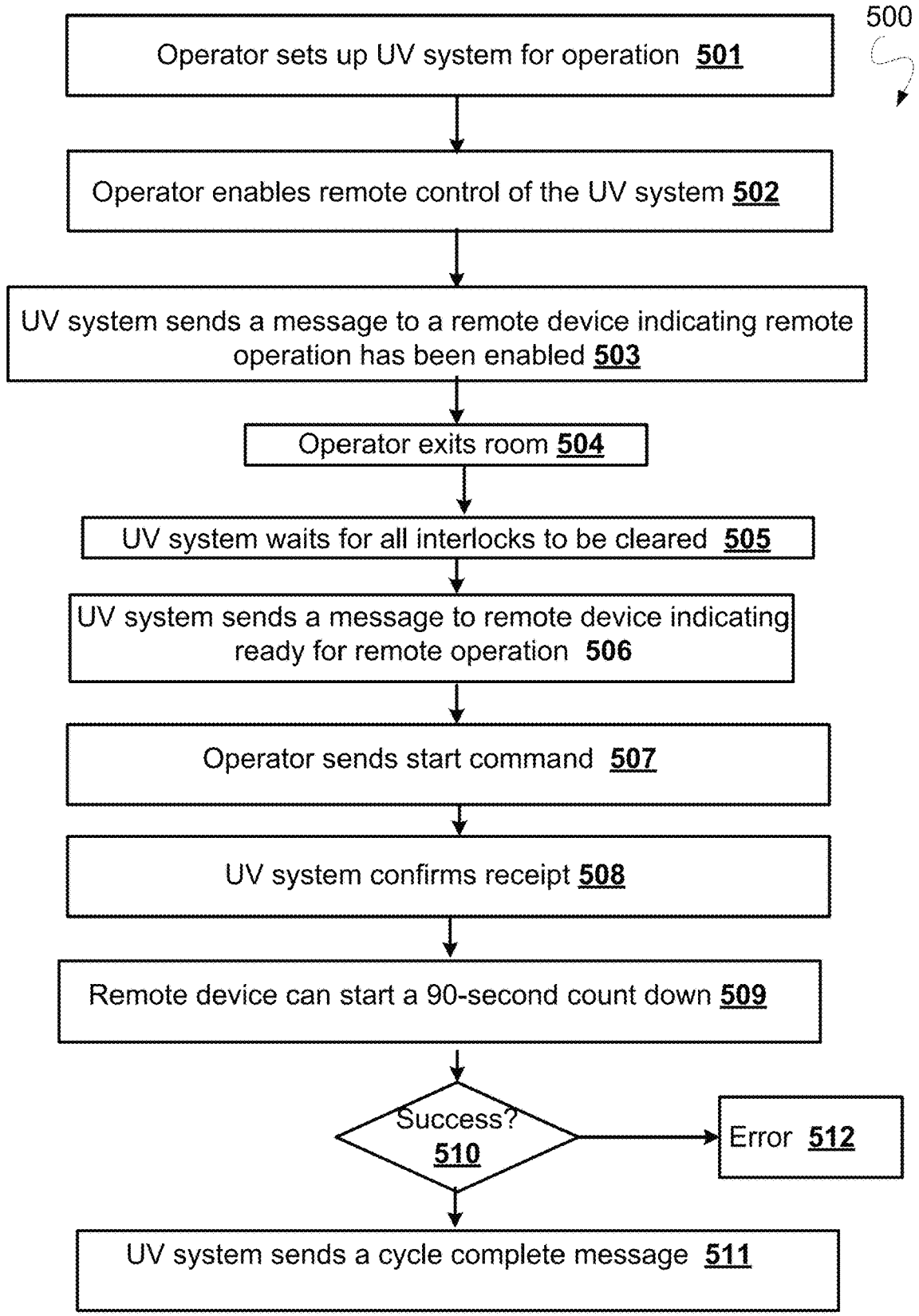
FIG. 5A shows a flow chart of a remote operation sequence for operating a system, in accordance with one example of the present disclosure.

FIG. 5A shows a flow chart 500 of a remote operation sequence for operating the system remotely in accordance with one example of the present disclosure. An operator may set up a disinfection system such as a UV system for treating a target room or volume (501). For example, the operator may power up the UV system and enable a wireless communication module on the UV system. The operator may then enable remote control of the UV system (502). In one example, the UV system may have an on-device user panel. The user panel can include a touch screen control to allow the operator to enable the remote control. The UV system may then send a message to a remote device indicating the remote operation of the UV system is now enabled (503). An example of a code can be "MX ENABLED." In some cases, this transmission may take place in the form of a short message service (SMS) and also provide messages containing media in the form of video or images. Additionally or alternatively, the transmission may be through a WiFi for other wireless network to an App on the remote device, for example, the operator's smartphone device. Once confirmed, the operator may exit the room in which the UV system is set up for operation (504). This exit provides the operator the opportunity to control the UV system from outside the room and without exposure to the UV.

The UV system may then wait for all interlocks to be cleared (505). Here, a number of safety locks may be placed on the mechanical portions of the system to prevent accidental activation to expand the arms of the system. Examples of safety locks include but are not limited to emergency stop buttons, motion sensors, hinge sensors, scanners, or infrared detection systems. Once the interlocks are cleared, the UV system may send a message to the remote device indicating the UV system is now ready for remote operation (506). An example of a code can be "MX_RDY." This indication can provide the operator with the assurance that the system-level checks have been performed and the UV system is now verified for operation.

In response, the operator may send a start command to the UV system (507). For example, the start code be set by "SMS_START=ON; SMS_START=OFF." The UV system may then confirm receipt of the start code. In one example, the receipt code may be communicated by ""SMS_START=ON; SMS_START=OFF." While this example is provided in the form of a SMS format, other formats and WiFi protocols can also be used.

The remote device can then start a countdown for a specified cycle time for the system, for example, 90 second count down (509). Non-limiting example include, 15 seconds, 30 seconds, 45 seconds, 60 seconds, 75 seconds, 90 seconds, 120 seconds, 160 seconds, 300 seconds, or 600 seconds. The UV system may then operate to determine whether the operation is successful (510). If the UV system has completed a cycle successfully, the UV system may send a cycle complete message, for example by the code "MX_CMPLT." In case the UV system fails to complete the cycle successfully, the UV system may send an error message, for example, by the code "MX_ERR."

Figure 5B:
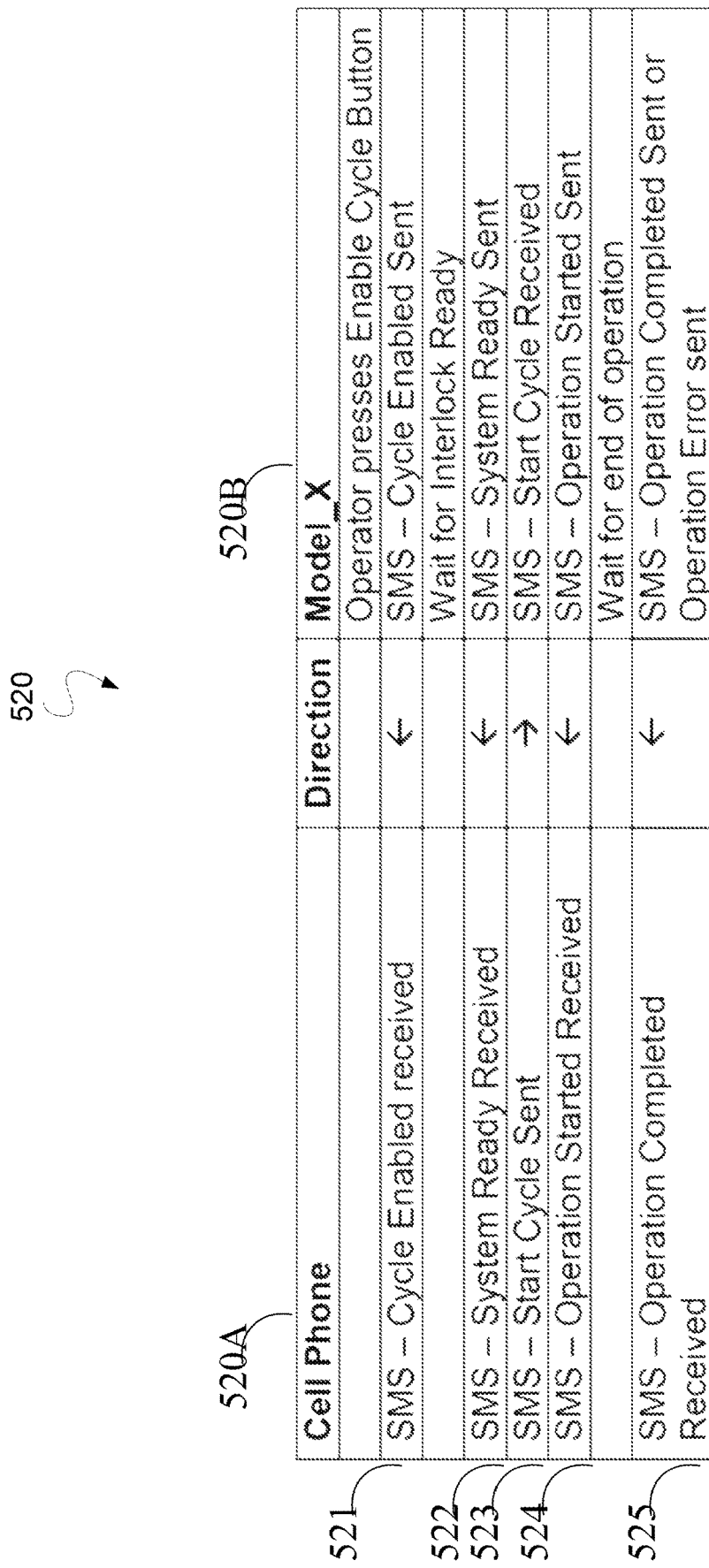
FIG. 5B illustrates a diagram of operations to drive a system from a remote source to allow for remote operation and monitoring, in accordance with one example of the present disclosure.

FIG. 5B illustrates a diagram 520 of operations to drive a system 520B from a remote source 520A to allow for remote operation and monitoring, in accordance with one example of the present disclosure. Here, system 520B can be a UV system noted by "Model X" and the remote source 520A can be a cellphone of the operator. Initially, the operator can press an enable cycle button on system 520B. This activation can trigger system 520B to send a message to remote source 520A, as illustrated in row 521. Thereafter, system 520B may wait for interlock on the system to be ready and cleared. Once cleared, system 520B may transmit a message to remote source 520A that the system is ready, as illustrated in row 522. In response, remote source 520A may transmit a message to system 520B to start cycle, as illustrated in row 523. When the system initiates the cycle, the system 520B may transmit a message to the remote source 520A that the operation has started, as illustrated in row 524. The system 520B may then wait for the end of the operation. Once the operation is completed, the system 520B may transmit a message to the remote source 520A that the operation has been completed, as illustrated in row 525. Additionally, if the operation falls through, the system 520B may transmit a message to the remote source 520A about the operation error.

Figure 5C:
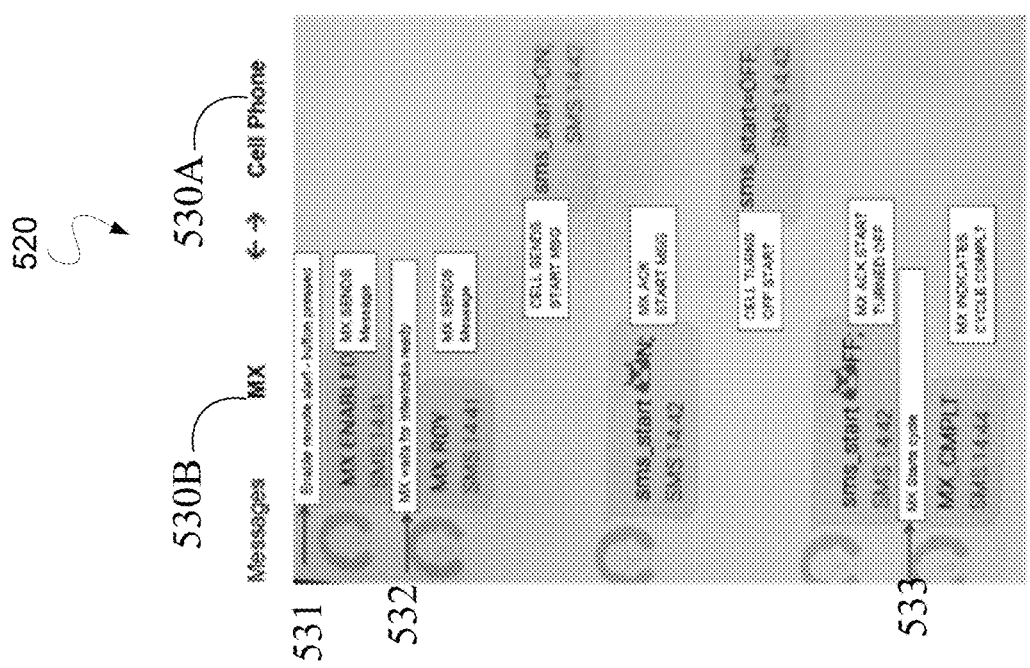
FIG. 5C illustrates a sequence of text message codes to remotely operate and monitor a system, in accordance with one example of the present disclosure.

FIG. 5C shows a screenshot 530 illustrating a sequence of text message codes to remotely operate and monitor a system 530B from a cell phone 530A, in accordance with one example of the present disclosure. Here, the system 530B is initially enabled for remote operation (531). The system 530B sends a message to cell phone 530A. Thereafter, the system 530B waits for interlocks on the system to be ready and cleared (532). Once cleared, the system 530B transmits a message to cell phone 530A that the system is ready.

Once received, cell phone 530A transmits a message to system 530B to start an operation. In response, system 530B may acknowledge receipt and will start an operation cycle (533). Once the cycle is successfully completed, the system 530B may send a message to cell phone 530A that the cycle is complete.

Figure 6:
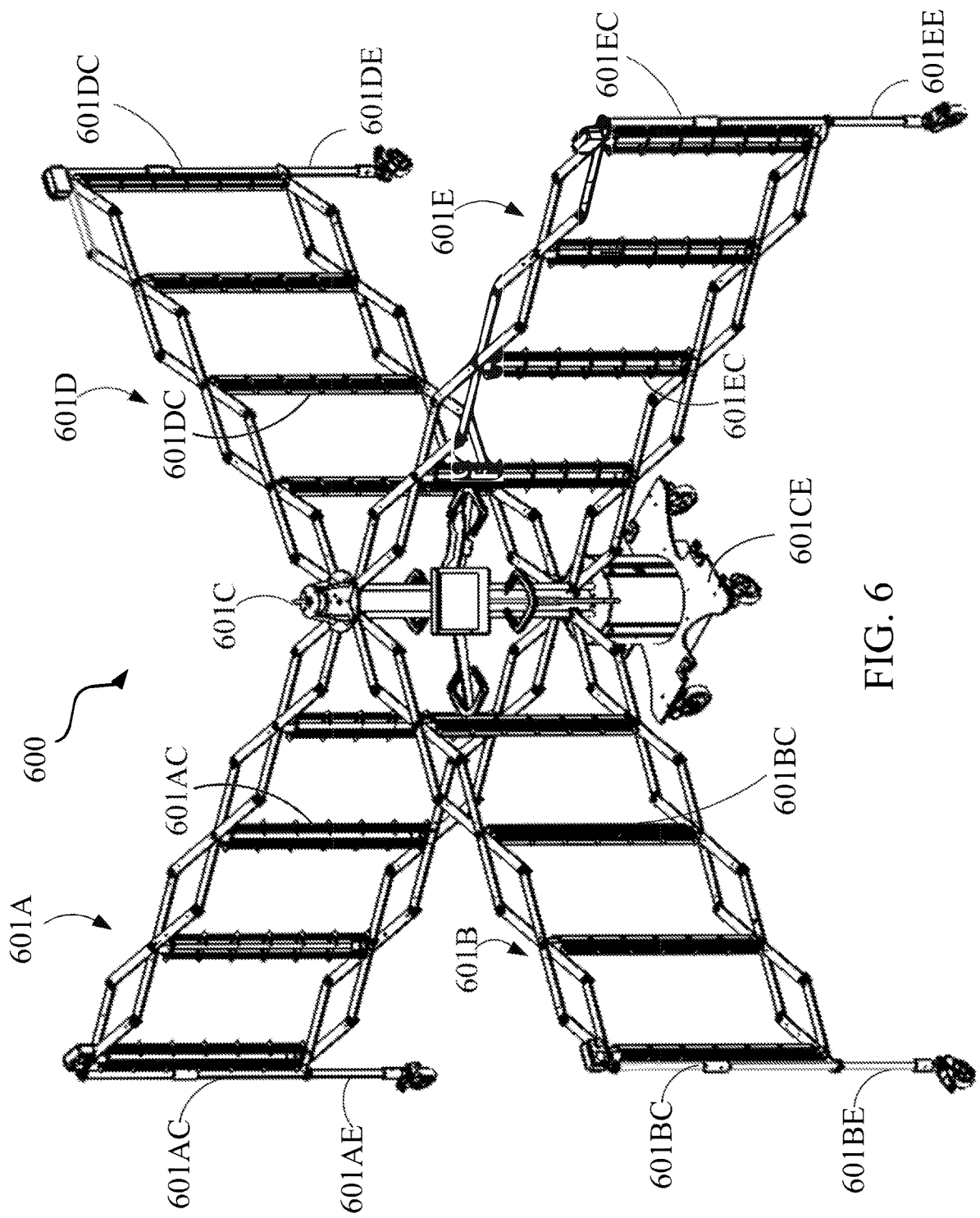
FIG. 6 illustrates a perspective view of a set of expandable arms each including a horizontal scissors arms, in accordance with one example of the present disclosure.

FIG. 6 shows a diagram 600 illustrating the horizontal scissor mechanisms on each expandable arm of a system. As illustrated, the system includes four expandable arms, namely, 601A, 601B, 601D, and 601E. Each expandable arm includes four horizontal scissor mechanisms linked in a chain. The system also includes a center column 601C that includes a vertical pole mounted on a movable base 601CE. The expandable arms are connected to the center column 601C. Expandable arms 601A, 601B, 601D, and 601E respectively includes bases 601AE, 601BE, 601DE, and 601EE. UV light sources can be mounted on each expandable arm at, for example, columns 601AC, 601BC, 601DC, and 601EC. These horizontal scissors mechanisms can improve stability to the UV light sources. These horizontal scissors mechanisms can also help define and create proportionality distances between each UV light source. Specifically, as the scissors mechanisms are expanded from or contracted to the center column 601C, the spacing between the UV light sources changes in proportionally to one another and provides even, repeatable, and uniform distribution of irradiance throughout the space. In some cases, the UV light sources can be vertically mounted on columns 601AC, 601BC, 601DC, and 601EC. Additionally or alternatively, the UV light sources can also be horizontally mounted on each expandable arm.

Figure 7B:
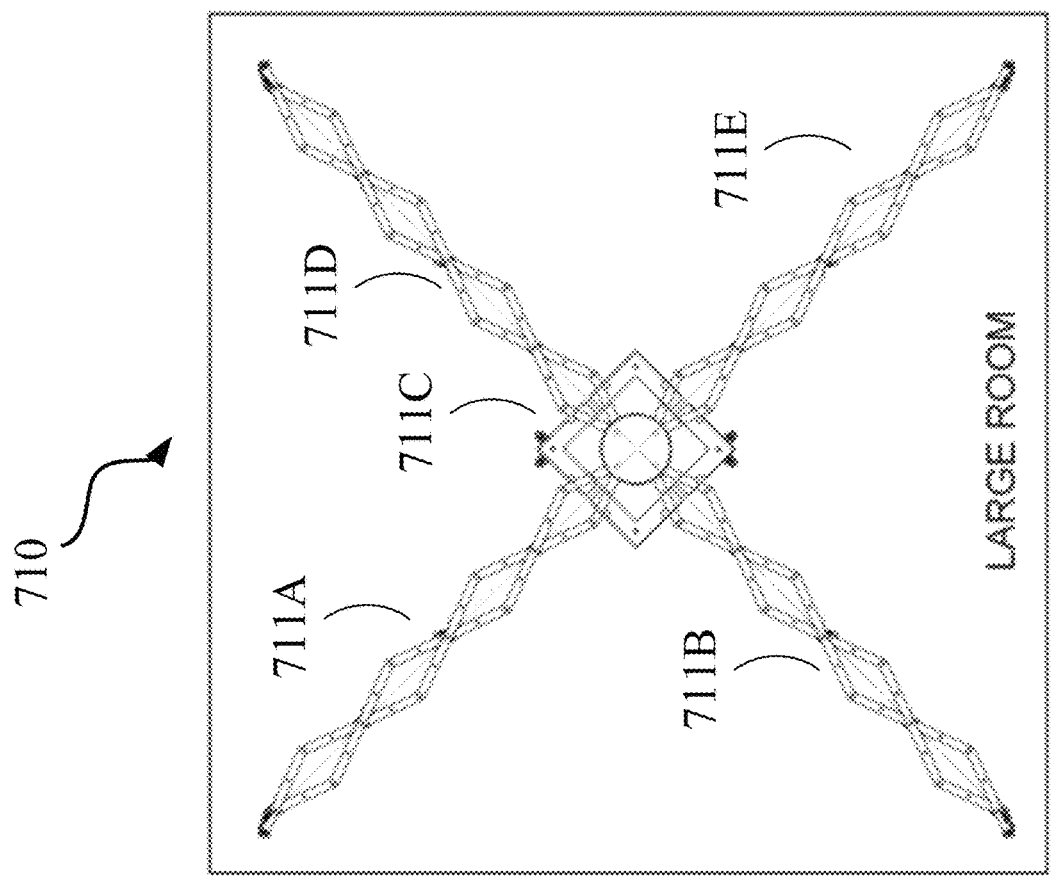
FIGS. 7A and 7B provide a top view illustrating a system capable of transitioning between a fully collapsed position and a fully expanded position, in accordance with one example of the present disclosure.
Figure 7A:
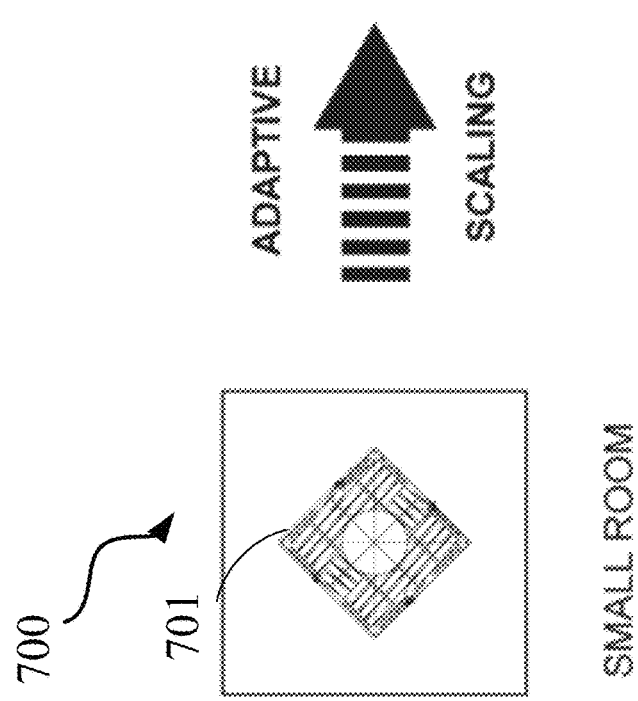

FIG. 7A shows a diagram 700 illustrating an exemplary system transforming from a first position 701 to a second position 710, which is illustrated in FIG. 7B. In the first position 701, all four expandable arms, namely, 711A, 711B, 711C, and 711D are fully collapsed around center column 711C. In the second position 710, all four expandable arms, namely, 711A, 711B, 711C, and 711D are fully unfolded from center column 711C. Thus, the diagram 700 demonstrates that an exemplary device can be adaptively scaled to fit a room of various size and shape because the exemplary device can expand from the minimum size, for a small room, to the fully extended maximum size for a large room.

To create these horizontal scissor mechanisms, custom bushings can be used at each hinge point to create uniform motion between the linkages. The rotatable and expandable scissor arms can allow the exemplary device to be adaptively scaled to match the size and shape of any type of room in healthcare facilities. The scaling of the exemplary device to different rooms can enforce an irradiance field with adequate levels of relatively homogenous irradiance to various areas of a room.

In order to transport the system, the horizontal scissor arms can be locked into place within a center base. This can be achieved with a hidden locking mechanism 900 within a vertical shaft 901 having an outer diameter. In some embodiments, the hidden locking mechanism 900 can include a collar 902 disposed about the vertical shaft 901, as shown in FIGS. 9A and 9B. In such an embodiment, the collar 902 can have an inner diameter that is large enough to fit about the outer diameter of the vertical shaft 901 and allow the collar 902 to slide along the vertical shaft 901. The collar 902 can additionally have an outer diameter that is larger than the outer diameter of the vertical shaft. In some embodiments, the hidden locking mechanism 900 can include two sections. For example, when a top section is pulled up along the vertical shaft, a corresponding bottom section can also be lifted up, allowing for only the vertical shaft 901 to be exposed which can be small enough to clear the center base locking section. In order to lock the arms into place, the vertical shaft 901 can be pushed into a cut out section in the center base, and the collar 902 can be lowered or can fall with gravity, allowing the arm to be secured.

Figure 10A:
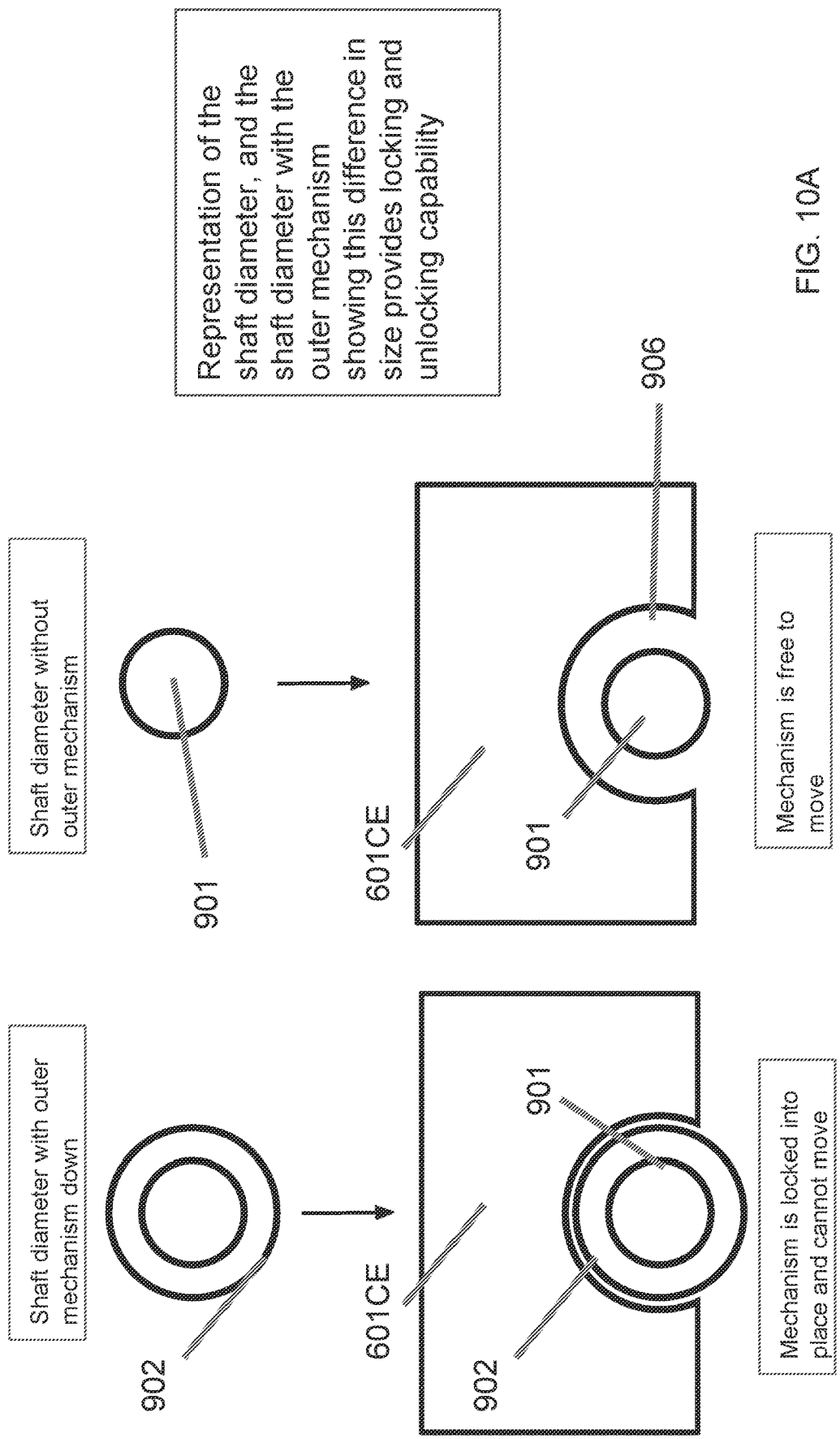
FIG. 10A illustrates top views representing a locking mechanism in unlocked and locked positions, in accordance with one example of the present disclosure.
Figure 10B:
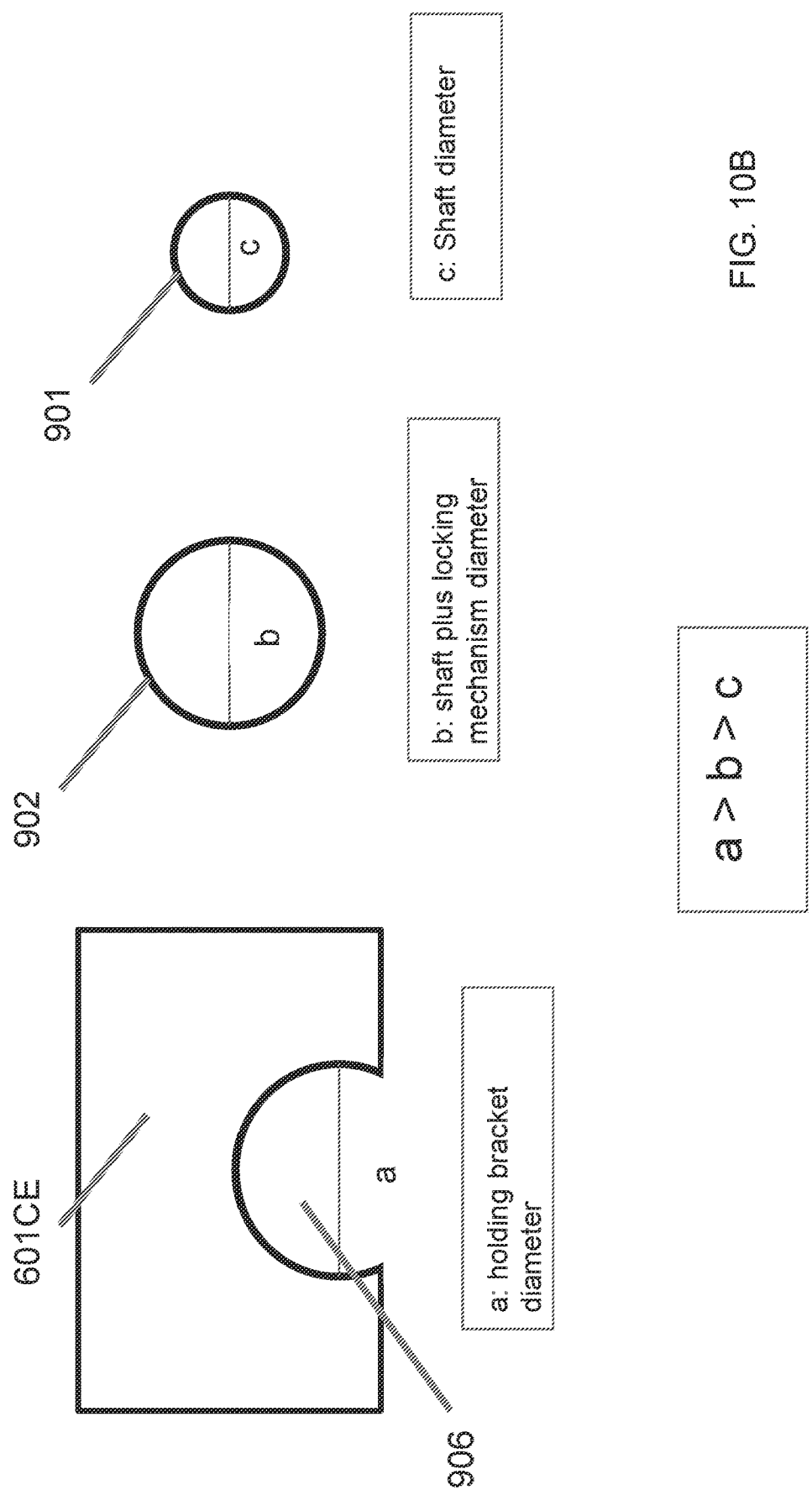
FIG. 10B illustrates top views of showing diameters of components of the locking mechanism, in accordance with one example of the present disclosure.

In another aspect, some implementations provide a system, e.g. system 600 as shown in FIG. 6, that includes: a structure configurable to irradiate a target volume, wherein the structure includes: a movable base 601CE including a holding bracket 904, e.g., movable base 601CE having a slot 906; a plurality of arms 601A, 601B, 601D, and 601E connected to an anchor surface, e.g. center column 601C, each arm 601A-D configurable between a first position and a second position, wherein the arm 601A-D is fully collapsed in the first position and fully expanded in the second position; a support 601AC, 601BC, 601DC, and 601EC connected to at least one arm of the plurality of arms, the support including an inner shaft, or vertical shaft, e.g., vertical shaft 901, capable of radially fitting into the slot 906 of the holding bracket 904; and a collar 902 connected to the support 901 and axially adjustable within the slot 906 of the holding bracket 601CE. The holding bracket 601CE, as seen in FIGS. 10A and 10B, can be configured to restrict a movement of the collar, and thus the arm, to within the slot 906 of the holding bracket 601CE, as the inner diameter a of the slot is larger than the outer diameter b of the collar 902. The arms 601AC, 601BC, 601DC, 601EC can be fixed within the slot 906 because the outer diameter b of the collar 902 can be larger than the size of the opening of the slot, as seen in FIG. 10A. When the collar 902 is lifted above the slot 906, the outer diameter of the vertical shaft 901 can be smaller than the opening of the slot 906 to allow the arms 601AC, 601BC, 601DC, 601EC to eb withdrawn from the holding bracket 601CE. The system can additionally include a plurality of light sources connected to the plurality of arms and capable of emitting ultraviolet light to irradiate the target volume when the arms of the structure are positioned in-between the first position and the second position.

As the device can be adaptive to many types of rooms, shapes and sizes, an adaptive mapping of motion sensors can be used. This can be achieved with a 360 degree sensor at the center of an exemplary device and corresponding sensors at the end of each adaptive arm. The 360 degree sensor can indicate if there is any motion within its view from a range of angles. The peripheral sensors can cover any additional alcoves, doorways, or other configurations of rooms that may not be visible to the center sensor.

As the device will deploy and fill an entire volume of space, it will also be useful to remote operation and monitoring. This chain of events between the remote device and the unit is illustrated in FIGS. 7A and 7B.

Figure 8:
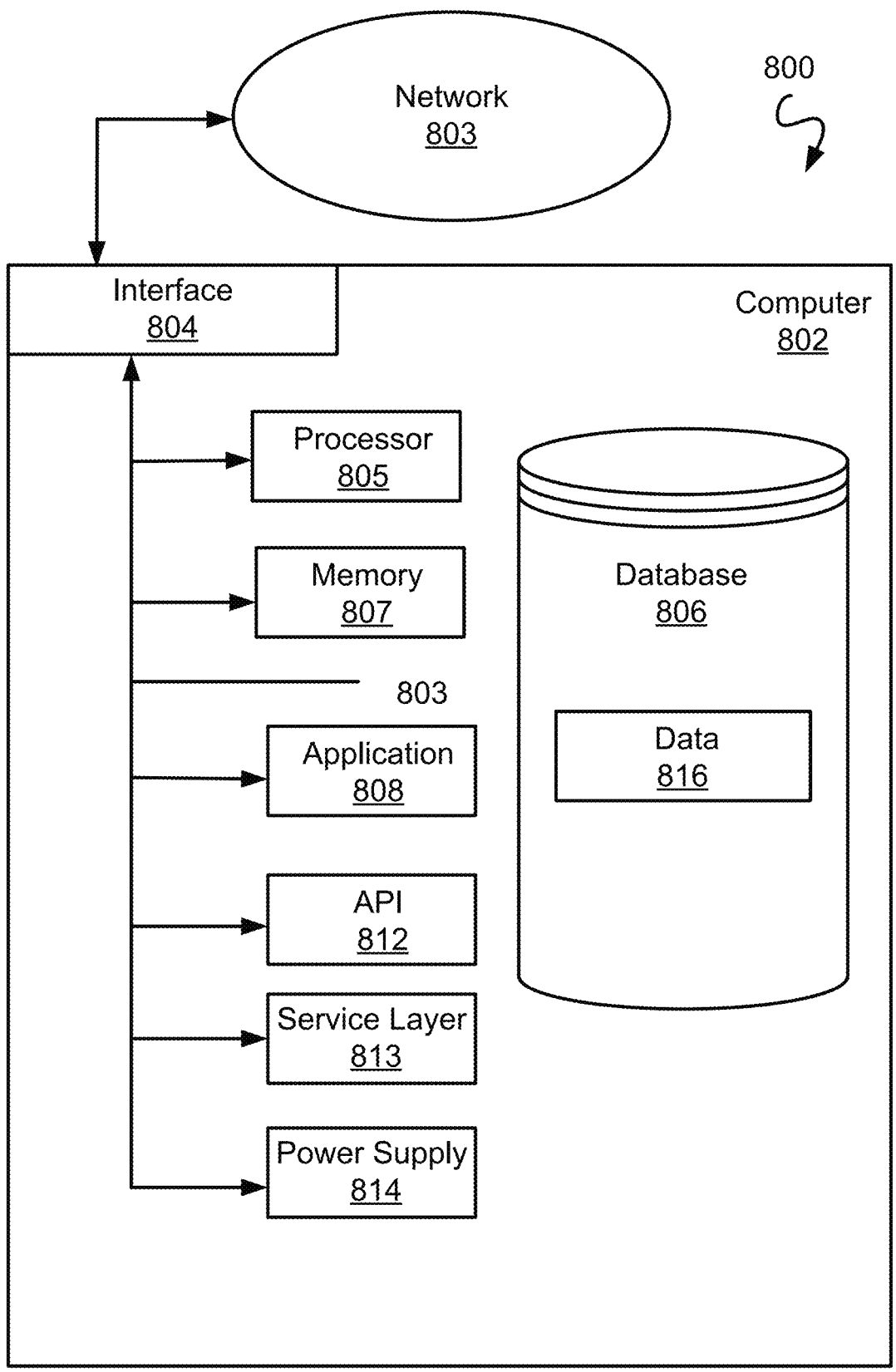
FIG. 8 is a block diagram illustrating an example of a computer system used to provide computational functionalities associated with described algorithms, methods, functions, processes, flows, and procedures, according to an implementation of the present disclosure.

FIG. 8 is a block diagram illustrating an example of a computer system 800 used to provide computational functionalities associated with described algorithms, methods, functions, processes, flows, and procedures, according to an implementation of the present disclosure. The illustrated computer 802 is intended to encompass any computing device such as a server, desktop computer, laptop/notebook computer, wireless data port, smart phone, personal data assistant (PDA), tablet computing device, one or more processors within these devices, another computing device, or a combination of computing devices, including physical or virtual instances of the computing device, or a combination of physical or virtual instances of the computing device. Additionally, the computer 802 can comprise a computer that includes an input device, such as a keypad, keyboard, touch screen, another input device, or a combination of input devices that can accept user information, and an output device that conveys information associated with the operation of the computer 802, including digital data, visual, audio, another type of information, or a combination of types of information, on a graphical-type user interface (UI) (or GUI) or other UI.

The computer 802 can serve in a role in a computer system as a client, network component, a server, a database or another persistency, another role, or a combination of roles for performing the subject matter described in the present disclosure. The illustrated computer 802 is communicably coupled with a network 803. In some implementations, one or more components of the computer 802 can be configured to operate within an environment, including cloud-computing-based, local, global, another environment, or a combination of environments.

The computer 802 is an electronic computing device operable to receive, transmit, process, store, or manage data and information associated with the described subject matter. According to some implementations, the computer 802 can also include or be communicably coupled with a server, including an application server, e-mail server, web server, caching server, streaming data server, another server, or a combination of servers.

The computer 802 can receive requests over network 803 (for example, from a client software application executing on another computer 802) and respond to the received requests by processing the received requests using a software application or a combination of software applications. In addition, requests can also be sent to the computer 802 from internal users, external or third-parties, or other entities, individuals, systems, or computers.

Each of the components of the computer 802 can communicate using a system bus 803. In some implementations, any or all of the components of the computer 802, including hardware, software, or a combination of hardware and software, can interface over the system bus 803 using an application programming interface (API) 812, a service layer 813, or a combination of the API 812 and service layer 813. The API 812 can include specifications for routines, data structures, and object classes. The API 812 can be either computer-language independent or dependent and refer to a complete interface, a single function, or even a set of APIs. The service layer 813 provides software services to the computer 802 or other components (whether illustrated or not) that are communicably coupled to the computer 802. The functionality of the computer 802 can be accessible for all service consumers using this service layer. Software services, such as those provided by the service layer 813, provide reusable, defined functionalities through a defined interface. For example, the interface can be software written in JAVA, C++, another computing language, or a combination of computing languages providing data in extensible markup language (XML) format, another format, or a combination of formats. While illustrated as an integrated component of the computer 802, alternative implementations can illustrate the API 812 or the service layer 813 as stand-alone components in relation to other components of the computer 802 or other components (whether illustrated or not) that are communicably coupled to the computer 802. Moreover, any or all parts of the API 812 or the service layer 813 can be implemented as a child or a sub-module of another software module, enterprise application, or hardware module without departing from the scope of the present disclosure.

The computer 802 includes an interface 804. Although illustrated as a single interface 804 in FIG. 8, two or more interfaces 804 can be used according to particular needs, desires, or particular implementations of the computer 802. The interface 804 is used by the computer 802 for communicating with another computing system (whether illustrated or not) that is communicatively linked to the network 803 in a distributed environment. Generally, the interface 804 is operable to communicate with the network 803 and comprises logic encoded in software, hardware, or a combination of software and hardware. More specifically, the interface 804 can comprise software supporting one or more communication protocols associated with communications such that the network 803 or interface's hardware is operable to communicate physical signals within and outside of the illustrated computer 802.

The computer 802 includes a processor 805. Although illustrated as a single processor 805 in FIG. 8, two or more processors can be used according to particular needs, desires, or particular implementations of the computer 802. Generally, the processor 805 executes instructions and manipulates data to perform the operations of the computer 802 and any algorithms, methods, functions, processes, flows, and procedures as described in the present disclosure.

The computer 802 also includes a database 806 that can hold data for the computer 802, another component communicatively linked to the network 803 (whether illustrated or not), or a combination of the computer 802 and another component. For example, database 806 can be an in-memory, conventional, or another type of database storing data consistent with the present disclosure. In some implementations, database 806 can be a combination of two or more different database types (for example, a hybrid in-memory and conventional database) according to particular needs, desires, or particular implementations of the computer 802 and the described functionality. Although illustrated as a single database 806 in FIG. 8, two or more databases of similar or differing types can be used according to particular needs, desires, or particular implementations of the computer 802 and the described functionality. While database 806 is illustrated as an integral component of the computer 802, in alternative implementations, database 806 can be external to the computer 802. As illustrated, the database 806 holds the previously described data 816 including, for example, multiple streams of data from various sources, such as the motion sensors, the camera, and other monitoring devices on the UV light system as outlined in FIGS. 4D and 6.

The computer 802 also includes a memory 807 that can hold data for the computer 802, another component or components communicatively linked to the network 803 (whether illustrated or not), or a combination of the computer 802 and another component. Memory 807 can store any data consistent with the present disclosure. In some implementations, memory 807 can be a combination of two or more different types of memory (for example, a combination of semiconductor and magnetic storage) according to particular needs, desires, or particular implementations of the computer 802 and the described functionality. Although illustrated as a single memory 807 in FIG. 8, two or more memories 807 or similar or differing types can be used according to particular needs, desires, or particular implementations of the computer 802 and the described functionality. While memory 807 is illustrated as an integral component of the computer 802, in alternative implementations, memory 807 can be external to the computer 802.

The application 808 is an algorithmic software engine providing functionality according to particular needs, desires, or particular implementations of the computer 802, particularly with respect to functionality described in the present disclosure. For example, application 808 can serve as one or more components, modules, or applications. Further, although illustrated as a single application 808, the application 808 can be implemented as multiple applications 808 on the computer 802. In addition, although illustrated as integral to the computer 802, in alternative implementations, the application 808 can be external to the computer 802.

The computer 802 can also include a power supply 814. The power supply 814 can include a rechargeable or non-rechargeable battery that can be configured to be either user- or non-user-replaceable. In some implementations, the power supply 814 can include power-conversion or management circuits (including recharging, standby, or another power management functionality). In some implementations, the power-supply 814 can include a power plug to allow the computer 802 to be plugged into a wall socket or another power source to, for example, power the computer 802 or recharge a rechargeable battery.

There can be any number of computers 802 associated with, or external to, a computer system containing computer 802, each computer 802 communicating over network 803. Further, the term "client," "user," or other appropriate terminology can be used interchangeably, as appropriate, without departing from the scope of the present disclosure. Moreover, the present disclosure contemplates that many users can use one computer 802, or that one user can use multiple computers 802.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs, that is, one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal, for example, a machine-generated electrical, optical, or electromagnetic signal that is generated to encode information for transmission to a receiver apparatus for execution by a data processing apparatus. The computer-storage medium can be a machine-readable storage device, a machine-readable storage substrate, a random or serial access memory device, or a combination of computer-storage mediums. Configuring one or more computers means that the one or more computers have installed hardware, firmware, or software (or combinations of hardware, firmware, and software) so that when the software is executed by the one or more computers, particular computing operations are performed.

The term "real-time," "real time," "realtime," "real (fast) time (RFT)," "near(ly) real-time (NRT)," "quasi real-time," or similar terms (as understood by one of ordinary skill in the art), means that an action and a response are temporally proximate such that an individual perceives the action and the response occurring substantially simultaneously. For example, the time difference for a response to display (or for an initiation of a display) of data following the individual's action to access the data can be less than 1 millisecond (ms), less than 1 second (s), or less than 5 s. While the requested data need not be displayed (or initiated for display) instantaneously, it is displayed (or initiated for display) without any intentional delay, taking into account processing limitations of a described computing system and time required to, for example, gather, accurately measure, analyze, process, store, or transmit the data.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be, or further include special purpose logic circuitry, for example, a central processing unit (CPU), an FPGA (field programmable gate array), or an ASIC (application-specific integrated circuit). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with an operating system of some type, for example LINUX, UNIX, WINDOWS, MAC OS, ANDROID, IOS, another operating system, or a combination of operating systems.

A computer program, which can also be referred to or described as a program, software, a software application, a unit, a module, a software module, a script, code, or other component can be written in any form of programming language, including compiled or interpreted languages, or declarative or procedural languages, and it can be deployed in any form, including, for example, as a stand-alone program, module, component, or subroutine, for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network.

While portions of the programs illustrated in the various figures can be illustrated as individual components, such as units or modules, that implement described features and functionality using various objects, methods, or other processes, the programs can instead include a number of sub-units, sub-modules, third-party services, components, libraries, and other components, as appropriate. Conversely, the features and functionality of various components can be combined into single components, as appropriate. Thresholds used to make computational determinations can be statically, dynamically, or both statically and dynamically determined.

Described methods, processes, or logic flows represent one or more examples of functionality consistent with the present disclosure and are not intended to limit the disclosure to the described or illustrated implementations, but to be accorded the widest scope consistent with described principles and features. The described methods, processes, or logic flows can be performed by one or more programmable computers executing one or more computer programs to perform functions by operating on input data and generating output data. The methods, processes, or logic flows can also be performed by, and apparatus can also be implemented as, special purpose logic circuitry, for example, a CPU, an FPGA, or an ASIC.

Computers for the execution of a computer program can be based on general or special purpose microprocessors, both, or another type of CPU. Generally, a CPU will receive instructions and data from and write to a memory. The essential elements of a computer are a CPU, for performing or executing instructions, and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable memory storage device.

Non-transitory computer-readable media for storing computer program instructions and data can include all forms of media and memory devices, magnetic devices, magneto optical disks, and optical memory device. Memory devices include semiconductor memory devices, for example, random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Magnetic devices include, for example, tape, cartridges, cassettes, internal/removable disks. Optical memory devices include, for example, digital video disc (DVD), CD-ROM, DVD+/−R, DVD-RAM, DVD-ROM, HD-DVD, and BLURAY, and other optical memory technologies. The memory can store various objects or data, including caches, classes, frameworks, applications, modules, backup data, jobs, web pages, web page templates, data structures, database tables, repositories storing dynamic information, or other appropriate information including any parameters, variables, algorithms, instructions, rules, constraints, or references. Additionally, the memory can include other appropriate data, such as logs, policies, security or access data, or reporting files. The processor and the memory can be supplemented by, or incorporated in, special purpose logic circuitry.

To provide for interaction with a user, implementations of the subject matter described in this specification can be implemented on a computer having a display device, for example, a CRT (cathode ray tube), LCD (liquid crystal display), LED (Light Emitting Diode), or plasma monitor, for displaying information to the user and a keyboard and a pointing device, for example, a mouse, trackball, or trackpad by which the user can provide input to the computer. Input can also be provided to the computer using a touchscreen, such as a tablet computer surface with pressure sensitivity, a multi-touch screen using capacitive or electric sensing, or another type of touchscreen. Other types of devices can be used to interact with the user. For example, feedback provided to the user can be any form of sensory feedback. Input from the user can be received in any form, including acoustic, speech, or tactile input. In addition, a computer can interact with the user by sending documents to and receiving documents from a client computing device that is used by the user.

The term "graphical user interface," or "GUI," can be used in the singular or the plural to describe one or more graphical user interfaces and each of the displays of a particular graphical user interface. Therefore, a GUI can represent any graphical user interface, including but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a Web browser through which a user can interact with an implementation of the subject matter described in this specification, or any combination of one or more such back-end, middleware, or front-end components. The components of the system can be interconnected by any form or medium of wireline or wireless digital data communication (or a combination of data communication), for example, a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n or 802.20 (or a combination of 802.11x and 802.20 or other protocols consistent with the present disclosure), all or a portion of the Internet, another communication network, or a combination of communication networks. The communication network can communicate with, for example, Internet Protocol (IP) packets, Frame Relay frames, Asynchronous Transfer Mode (ATM) cells, voice, video, data, or other information between networks addresses.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of what can be claimed, but rather as descriptions of features that can be specific to particular implementations. Certain features that are described in this specification in the context of separate implementations can also be implemented, in combination, in a single implementation. Conversely, various features that are described in the context of a single implementation can also be implemented in multiple implementations, separately, or in any sub-combination. Moreover, although previously described features can be described as acting in certain combinations and even initially claimed as such, one or more features from a claimed combination can, in some cases, be excised from the combination, and the claimed combination can be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations can be considered optional), to achieve desirable results. In certain circumstances, multitasking or parallel processing (or a combination of multitasking and parallel processing) can be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

The invention claimed is:

1. A system comprising:
    a structure configurable to irradiate a target volume, wherein the structure includes:
    a movable base including a holding bracket having a slot;
    a plurality of arms connected to an anchor surface, each arm configurable between a first position and a second position, wherein the arm is fully collapsed in the first position and fully expanded in the second position;
    a support connected to at least one arm of the plurality of arms, the support including an inner shaft capable of radially fitting into the slot of the holding bracket; and
    a collar connected to the support and axially adjustable within the slot of the holding bracket, wherein the holding bracket is configured to restrict a radial movement of the collar to within the slot of the holding bracket; and
    a plurality of light sources connected to the plurality of arms and capable of emitting ultraviolet light to irradiate the target volume when the arms of the structure are positioned in-between the first position and the second position.

2. The system of claim 1, wherein the plurality of arms are connected to a center column disposed on the moveable base.

3. The system of claim 1, wherein the plurality of arms are capable of expanding and contracting independently of one another.

4. The system of claim 1, wherein the plurality of arms are capable of rotating around a fixed axis independently of one another.

5. The system of claim 1, wherein the plurality of arms each have a rotational range of up to 360 degrees.

6. The system of claim 1, wherein the plurality of light sources are split between two or more sets of horizontal scissors arms of each of the plurality of arms, wherein the two or more sets of horizontal scissors arms are of identical size and shape.

7. The system of claim 6, wherein the two or more sets of horizontal scissors arms are configured to move in unison when each arm is expanding from the first position to the second position.

8. The system of claim 7, wherein the two or more sets of horizontal scissors arms of each arm are connected at a matching set of intersections such that the fixed proportionality with respect to the spacing of the plurality of light sources are maintained when the arm is transitioning between the first position and the second position.

9. The system of claim 8, the matching set of intersections include bushings that facilitate each arm in transitioning between the first position and the second position.

* * * * *